United States Patent [19]
Hostettler et al.

[11] Patent Number: 6,120,904
[45] Date of Patent: *Sep. 19, 2000

[54] MEDICAL DEVICE COATED WITH INTERPENETRATING NETWORK OF HYDROGEL POLYMERS

[75] Inventors: Fritz Hostettler; David Rhum; Michael R. Forman; Michael N. Helmus; Ni Ding, all of New York, N.Y.

[73] Assignee: Schneider (USA) Inc., Plymouth, Minn.

[ * ] Notice: This patent is subject to a terminal disclaimer.

[21] Appl. No.: 09/317,531

[22] Filed: May 24, 1999

Related U.S. Application Data

[63] Continuation of application No. 08/382,318, Feb. 1, 1995, Pat. No. 5,919,570.

[51] Int. Cl.[7] .................................................. B32B 27/40
[52] U.S. Cl. ................................... 428/423.3; 428/423.5; 428/423.7; 428/424.8; 428/425.8; 525/452; 525/453; 604/96
[58] Field of Search .............................. 428/423.1, 423.3, 428/423.5, 423.7, 424.8, 425.8; 604/96; 525/452, 453

[56] References Cited

U.S. PATENT DOCUMENTS

| | | | |
|---|---|---|---|
| 4,100,309 | 7/1978 | Micklus et al. | 428/425 |
| 4,118,354 | 10/1978 | Harada et al. | 524/711 |
| 4,119,094 | 10/1978 | Micklus et al. | 428/425 |
| 4,307,004 | 12/1981 | Schuhmacher et al. | 428/423.1 |
| 4,373,009 | 2/1983 | Winn | 428/424.4 |
| 4,459,317 | 7/1984 | Lambert | 428/424.4 |
| 4,487,808 | 12/1984 | Lambert | 428/423.1 |
| 4,585,666 | 4/1986 | Lambert | 428/424.4 |
| 4,642,267 | 2/1987 | Creasy et al. | 428/413 |
| 4,666,437 | 5/1987 | Lambert | 428/424.4 |
| 4,801,475 | 1/1989 | Halpern et al. | 427/338 |
| 4,835,003 | 5/1989 | Becker et al. | 428/423.3 |
| 4,894,428 | 1/1990 | Thoma et al. | 428/423.1 |
| 4,906,237 | 3/1990 | Johansson et al. | 604/265 |
| 4,959,074 | 9/1990 | Halpern et al. | 623/66 |
| 4,990,357 | 2/1991 | Karakelle et al. | 427/2 |
| 5,023,114 | 6/1991 | Halpern et al. | 427/338 |
| 5,026,607 | 6/1991 | Kiezulas | 428/423.7 |
| 5,077,352 | 12/1991 | Elton | 525/409 |
| 5,112,736 | 5/1992 | Caldwell et al. | 435/6 |
| 5,132,108 | 7/1992 | Narayanan et al. | 424/78.17 |
| 5,179,174 | 1/1993 | Elton | 525/409 |
| 5,322,715 | 6/1994 | Jouck et al. | 427/409 |
| 5,569,706 | 10/1996 | Jacobs et al. | 428/423.1 |
| 5,576,072 | 11/1996 | Hostettler et al. | 427/532 |
| 5,662,960 | 9/1997 | Hostettler et al. | 427/2.3 |

FOREIGN PATENT DOCUMENTS

WO8909246  10/1989  WIPO .

*Primary Examiner*—Robert Dawson
*Assistant Examiner*—D. Aylward
*Attorney, Agent, or Firm*—Vidas, Arrett & Steinkraus

[57] ABSTRACT

A medical device comprising an organic polymer substrate material having a coating thereon, the coating comprising an interpenetrating network of two different hydrogel polymers, one of which is a polyurethane/polyurea hydrogel polymer, the polyurethane/polyurea hydrogel polymer being linked to the substrate material by covalent urea linkages.

7 Claims, No Drawings

MEDICAL DEVICE COATED WITH INTERPENETRATING NETWORK OF HYDROGEL POLYMERS

Continuation of Ser. No. 08/382,318, Feb. 1, 1995, U.S. Pat. No. 5,919,570.

BACKGROUND OF THE INVENTION

This invention relates generally to the field of synthetic polymeric coating compositions for polymeric and metal substrates, and more particularly, to coating compositions which are slippery and which exhibit tenacious adherence to the substrate to which they are applied, and to coated materials made therefrom. The coating compositions and coated substrate materials are biocompatible and suitable for use in medical devices which come in contact with various body fluids. Still more particularly, this invention relates to tenaciously adhering, slippery hydrogel coatings, on polymeric and metal substrates. The coatings are commingled hydrogels composed of a polyurethane/urea polymer hydrogel in combination with a poly(N-vinylpyrrolidone) polymer hydrogel. This invention also relates processes for making such commingled hydrogels, especially where the substrate materials to which they are applied are polymeric materials, which are intrinsically non-polar and hydrophobic. This invention further relates to a process whereby the surface of hydrophobic polymers are treated in order to render them more polar and hydrophilic so that the tenaciously adhering, slippery commingled hydrogel coatings of the present invention may subsequently be applied to the polymer surface. This invention still further relates to slippery-coated medical devices which are intended for insertion into a patient and which come in contact with various body fluids, particularly, blood.

In catheters and many other kinds of medical devices, it is often desirable to coat various plastic, rubber or metal parts thereof with products made from hydrophilic or certain other polymers that are lubricous and which produce low coefficients of friction during use. However, one of the problems associated with the utility of such coatings is their inability to remain intact and abrasion-resistant during clinical use in body fluids such as blood. Catheters used in angioplasty, gastroenterology and other medical specialties, are commonly made of polymeric materials which most often are relatively hydrophobic and not inherently slippery or biocompatible. Metal devices and components, such as guidewires, to which permanent adhesion of slip agents and/or hydrophilic polymers is often desired, present additional challenges. In any case, polymeric metallic substrates generally require some surface modification in order to reduce the friction between the catheter and other devices with which they work, such as vascular sheaths, and also to reduce the friction between the vasculature or other anatomical passageways and the catheter itself. Almost all currently used catheters have some form of surface modification or coating applied to them. The ability of the coating to reduce frictional resistance, its durability, as well as its biocompatibility are the most important aspects of an effectively coated surface.

Heretofore, catheters and other medical devices containing synthetic or natural polymers have often been coated with non-permanent compositions such as silicones and other slip agents, fluorocarbons, or hydrogels which, however, were usually not cohesively attached to the substrate surfaces. While such coatings can impart a low coefficient of friction to the surface of a medical device, they typically lack permanence with respect to frictional wear. Fluorocarbons, moreover, may peel or flake from the substrate, or when applied to a soft polymeric substrate material, may cause an increase in the stiffness of the material. In the case of marginally polar substrates used for the fabrication of catheters and other medical devices such as contact lenses, condoms, gastroenteric feed tubes, endotracheal tubes, and the like, a variety of polyurethane based compositions have been suggested as adhesive tie coats for affixing a double-coating on the substrates, but he results have been unsatisfactory because of the lack of suitable chemical moieties which can react fast enough with the isocyanate groups of the tie base coat intermediates to form covalent bonds having good cohesive characteristics to resist wear in clinical applications, such as on catheters used in coronary angioplasty. For such uses the coating must exhibit wear permanence, low coefficient of friction in contact with body fluids, as well extremely low toxicity and good biocompatibility. Whereas a number of polyurethane "tie coats" can improve adhesion to plastics and rubbers, they are oftentimes not compatible enough with respect to the polymer surface of the substrates to assure permanence of bonding for the intended medical application. Hydrophobic, non-polar, or only slightly polar polymer substrates are particularly difficult surfaces on which to attach durable coatings. In medical devices this can be a critical requirement for many clinical situations. Particular fields of medical specialties where such factors are important are enumerated below.

In Percutaneous Transluminal Coronary Angioplasty (PTCA) and Percutaneous Transluminal Angioplasty (PTA), the functional characteristics of balloon catheters include trackability through vasculature, crossability and recrossability of stenotic lesions, and retractability through the guiding catheter and the vascular sheath. These are dynamic functions that are fundamental to a successful and efficient interventional angioplasty procedure. They contribute to reduced trauma to the vasculature. In particular, recrossing of stenotic lesions is crucial to a successful outcome. High pressure angioplasty balloons, typically those made of polyethylene terephthalate (PET), can have problems with recrossability. This is because the relatively stiff PET material forms "wings" upon deflation after the first dilation. The winged profile of the deflated balloon can prevent recrossing of the stenotic lesion for a second dilatation. A durable slippery coating can aid in achieving recrossing of the lesion. Guiding catheters are better able to traverse tortuosity in the femoral artery and descending aorta with the help of a good slippery coating.

Stent catheters for use in vascular disease benefit from the characteristics imparted by a good slippery coating. Stent catheter delivery systems used in gastroenterology for opening of biliary passageways also benefit from a slippery coating with regard to traversing passageways leading to the site.

In coronary radiography, diagnostic catheters are used to deliver radiopaque fluid to the coronary arteries for visualization by x-ray fluoroscopy. These catheters benefit in the same way that guide catheters do from a good slippery coating, by aiding in traversing tortuosity in the femoral artery and the descending aorta.

U.S. Pat. Nos. 4,100,309 and 4,119,094 disclose the use of hydrophobic polyurethane polymer substrates with a polyvinylpyrrolidone (PVP) coating to form lubricious polyurethane-pyrrolidone interpolymers. When these materials are utilized as slippery materials for such devices as balloon catheters, the slippery outer coatings show only limited permanence in intravenous applications where they are exposed to blood.

U.S. Pat. No. 4,118,354 discloses the formation of polyurethane hydrogels which are reaction products of a polyisocyanate, having at least two isocyanate groups, and a polyether, produced from a plurality of alkylene oxides, 50 to 90% of which is ethylene oxide, added at random to a polyalcohol having at least two terminal hydroxyl groups, by the dispersal of the prepolymer reaction product into an aqueous liquid phase. Neither the formation of slippery hydrogel barrier coats upon plastic or metal substrates nor the affixation thereof to such substrates by means of covalent chemical bonds to assure durability of said coating upon exertion of dynamic forces thereon are described.

U.S. Pat. No. 4,373,009 describes a method for coating various polymeric substrates with polyurethane prepolymers containing free isocyanate groups and subjecting the thus coated substrates with a second coating of water-soluble copolymers of unsaturated monomers containing at least some isocyanate-reactive monomers as part of their backbone. It is postulated that the isocyanate treatment of the substrate results in firmly anchored tie coats even for polymers containing no isocyanate-reactive groups. No convincing evidence of covalent bonding of the urethane tie coat to the substrate is presented, nor is there any indication that the procedure is suitable for the use in critical medical devices where biocompatibility is a significant issue.

U.S. Pat. Nos. 4,459,317 and 4,487,808 disclose a process for treating a polymer substrate with a first coating of an isocyanate solution containing at least two unreacted isocyanate groups per molecule, and, optionally, a polymer; followed by a second coating of a high molecular weight polyethylene oxide, such that after curing of the isocyanate, the two coatings form a hydrophilic polyethylene oxide-polyurea interpolymer having a low coefficient of friction. Methods for applying a base coat of low molecular weight aromatic or aliphatic polyisocyanates dissolved in suitable organic solvents, followed by evaporating the solvent and then applying a second coat of a high molecular weight polyethyleneoxide polymer dissolved in an organic solvent are also disclosed. The second solution, which may also contain amine catalysts, is then evaporated and the two coatings are heated at elevated temperature in the presence of air which must contain enough moisture to react with the isocyanate of the first coating. The described processes are relatively time-consuming. The isocyanate coating is applied by spraying or dipping the substrate, and no evidence is presented that the isocyanate coating undergoes any reaction with the substrate surface to make it better adhering to the substrate surface. Medical devices made from a polymer substrate to which the coating has been applied, for use in body cavities, including especially the urethra, are also disclosed. Use of the coatings and coated medical devices in a blood medium, however, is not specifically disclosed, and it is believed that in the absence of bonding of the isocyanate coating to the substrate itself, the coatings and coated medical devices ultimately do not demonstrate the desired degree of permanence, especially in a blood environment.

U.S. Pat. No. 4,642,267 discloses a hydrophilic polymer blend which contains a thermoplastic polyurethane having no reactive isocyanate groups and a hydrophilic poly(N-vinyl lactam). The blend is said to be slippery in aqueous environments and is used as a low-friction coating for various substrates. Its use and performance in blood is not disclosed.

U.S. Pat. Nos. 4,585,666 and 4,666,437 disclose a method whereby a polymer substrate is first coated with a hydrophobic low molecular weight polyisocyanate containing at least two unreacted isocyanate groups per molecule, and, optionally, a polymer, dissolved in organic solvents; and, after solvent evaporation, is then coated with a solution containing polyvinylpyrrolidone and an amine catalyst, in organic solvents, such that after curing the isocyanate in atmospheric moisture, and curing at elevated temperature, the two coatings form a hydrophilic polyvinylpyrrolidone-polyurea interpolymer having a low coefficient of friction when wetted with a water-based liquid. The permanence of such coatings, when applied to substrates for catheters or balloons used in a blood medium, is however, not discussed. The process appears to be time-consuming and not cost-effective.

U.S. Pat. No. 4,835,003 discloses a method of coating medical tubing with a mixture of a hydrophilic polyurethane resin solution, a polyvinylpyrrolidone solution, and a $C_1$ to $C_3$ alcohol, to form a water-activated lubricating coating on the tubing. After immersion in water the coating becomes very slippery. No representation is made with regard to the wear permanence of the coating, especially in a blood environment.

Published PCT Patent Application WO 89/09246 describes the use of shaped structures having polymer or metal substrate surfaces coated with crosslinked hydrophilic polymers, such as polyvinylpyrrolidone. The coated structures are said to be durable and exhibit a low coefficient of friction when wet. The use of polyethylene terephthalate (PET) substrates, which are often used in balloons for angioplasty catheters, is described. Crosslinking between the substrate and the coating is achieved by subjecting a hydrophilic polymer deposited on the substrate to thermally activated free radical initiators, UV light activated free radical initiation, or E-beam radiation. The adherence of the crosslinked hydrophilic polymer to the substrate surface is beleived to be due to physical forces rather than to chemical bonding. A disadvantage of the process is that neither the thermally activated free radical initiators nor the UV initiators are biocompatible or suitable for medical uses. Furthermore, E-beam radiation applied to certain materials such as fluorocarbon polymers, which are often employed in medical devices, can be detrimental to these materials.

U.S. Pat. No. 4,990,357 describes coating compositions containing combinations of chain-extended hydrophilic thermoplastic polyetherurethane polymers with a variety of hydrophilic high molecular weight non-urethane polymers, such as polyvinylpyrrolidone. The coatings are made lubricious by contact with an aqueous liquid. The coatings adhere to a variety of polymeric substrates, including polyvinylchloride (PVC) and polyurethane (PU). A disadvantage of the coating compositions is that neither the thermoplastic polyurethane polymer, nor the hydrophilic non-urethane polymer can react with one another. Hence, it is not expected that these coatings give acceptable adhesion to most of the plastic substrates used in angioplasty devices.

U.S. Pat. No. 4,906,237 discloses the use of an osmolality-increasing compound such as glucose, sorbitol, sodium chloride, sodium citrate and sodium benzoate to improve the slipperiness and wetability of a surface coating for a polymeric substrate material which has first been coated with a non-reactive hydrophilic polymer. The coatings and coated substrates are said to be useful for situations where they come into contact with mucous membranes.

U.S. Pat. No. 5,026,607 describes the formation of a slippery coating of a urethane and a silicone or siloxane emulsion. A crosslinking agent, such as a polyfunctional aziridine, may be added to crosslink carboxyl functional groups in the coating with carboxyl functional groups on the substrate surface. The use of primers in the case of a PET substrate surface is also disclosed to effect better adhesion of the coating to the substrate. Alternative treatment methods to the use of primers, for example, the introduction of substrate surface functionality by means of plasma treatment or corona discharge to obtain hydroxyl, carboxyl, or amino functionality are also mentioned.

U.S. Pat. Nos. 5,077,352 and 5,179,174 describe the formation of lubricious coatings applied to a variety of substrates by means of forming crosslinked polyurethanes in the presence of polyethylene oxide polymers at high temperatures. No surface treatment of the substrate surfaces is described and the selection of the isocyanate compounds includes, in particular, reactive aromatic diisocyanates of the type not believed to be biocompatible. It is doubtful whether these methods can be recommended for use with intravenous catheter devices in view of the known carcinogenic nature of the amines which can result from the decomposition of such polyurethane polymers. Moreover, the high temperature polymerization procedures suggested can result in unacceptable physical changes of several of the polymer materials utilized in angioplasty catheters.

Similar drawbacks pertain to the methods and compositions described in U.S. Pat. No. 5,160,790 describing the use of the same type of polyurethane polymers with various PVP polymers as the hydrophilic polymer species.

U.S. Pat. Nos. 4,801,475 and 4,959,074 describe the application of an aqueous solution of a mucopolysacharide, dehydrating said film to dryness by various means, and then crosslinking the polysaccharide by the application of a catalyzed solution of an organic-soluble aliphatic polyisocyanate. No mention with respect to the formation of covalent bonds to the plastic substrates is made, and the suggested process is elaborate and time-consuming. No proof regarding permanent covalent bonding to non-polar plastic substrates is presented.

U.S. Pat. No. 5,023,114 describes a method of interlaminar grafting of two not mutually soluble polymers comprising coating an object with materials having functional groups capable of reacting with a mucopolysaccharide, and manifesting a high degree of adhesion to the object, removing solvent from said solution, then applying as a second coat an aqueous solution of a mucopolysaccharide and removing water from said second coat such as to form a continuous film, and thereupon chemically joining said first and second films by means of heat treatment. The patent does not teach the treatment of non-reactive surfaces prior to application of the first coating. Furthermore, it does not demonstrate the wear performance of such coatings combinations deposited on unreactive surfaces, nor does it teach the formation of "commingled" polymer structures by means of at least two hydrophilic polymer species which are compatible, but chemically dissimilar. Moreover, the method for the application of the coatings compositions requires a time-consuming and relatively inefficient technique of operation.

U.S. Pat. No. 5,132,108 discloses the use of plasma treatment of certain polymeric substrate surfaces, to introduce carboxyl and/or hydroxyl reactive groups thereon, utilizing an oxygen and water-containing plasma gas, followed by treating the resulting polymeric surface with a spacer component having amine groups. The treating step is conducted in the presence of a coupling agent, whereby covalent linkages are formed between the spacer component amine groups and the reactive sites of a modified hydrophilic polymeric substrate surface. Finally, an antithrombogenic, fibrinolytic or thrombolytic agent, such as heparin or other polysaccharides is contacted with the spacer component-treated modified polymeric surface. This method utilizes the introduction of relatively slow reacting carboxyl and/or hydroxyl groups onto the substrate surface, and encompasses too many processing steps for cost-effective production of medical devices. Although the resulting coated surfaces are biocompatible, they are not slippery and do not have low coefficients of friction.

U.S. Pat. No. 5,112,736 describes a method of introducing amino functionality on a variety of polymeric substrate surfaces, including polymers of polypropylene (PP), polyethylene (PE), polyvinylchloride (PVC), and polyvinylidenefluoride (PVDF), by plasma-treatment thereof in the presence of radiofrequency plasma discharge by means of ammonia, organic amine-containing gases, or mixtures of such plasma gases. The method is used for very hydrophobic hydrocarbon polymer articles such as PP membranes. It does not appear to give good results with PE polymers. PP films which contain amino groups on their surfaces are used for DNA sequencing on the membranes. No reference with respect to their use for attachment of hydrophilic PU polymers to highly hydrophobic substrates is made, nor does the reference disclose reliable methods to affix amino surface groups to PE surfaces which would be expected to work in the products and processes contemplated by the present invention.

Surprisingly, the drastic influence of the chemical and physical composition of body fluids upon the permanence of low friction coatings when exposed to dynamic forces in such liquids has heretofore not been recognized. Whereas many slippery coating additives such as relatively low molecular weight silicones and a variety of hydrophilic polymers exhibit good lubricity and relatively good permanence in the presence of water or saline solutions, they quickly lose their efficacy by exposure to dynamic forces in the presence of blood, a much more complex fluid composition.

Accordingly, there remains a need in the art of medical devices for an improved lubricious coating material that demonstrates wear permanence, combined with the characteristics of biocompatibility, low toxicity and low coefficient of friction in contact with body fluids, especially blood.

SUMMARY OF THE INVENTION

The covalently attached protective polyurethane-polyurea (PU/PUR) hydrogel coating and its combination with the structurally dissimilar second hydrogel polymer is slippery when wet and the intimately commingled hydrogel substrate surface exhibits excellent permanence and wear characteristics when exposed to dynamic forces in the presence of various body fluids, especially blood. Furthermore, these coatings, being derived from materials exhibiting essentially no toxic behavior in their hydrogel state, greatly enhance the biocompatibility of the resulting medical device during use and exhibit excellent adhesion to the plasma-treated substrate surfaces.

Medical devices and components therefor, fabricated from polymeric plastic substrates, are first plasma-treated with plasma gases containing nitrogen atoms, thereby forming amino groups on the plastic substrate surfaces. In the case of very hydrophobic plastic substrates, for example, various grades of polyethylenes, nylons 11 and 12, and the like, we have discovered that optimal results are achieved by combinations of various oxidative chemical treatments or oxygen-containing plasma treatments, followed by plasma exposure to nitrogen-containing plasma gases, or to gaseous ammonia or low-boiling amines, or mixtures thereof, to affix much more reactive amino groups onto the substrate surfaces. Extremely hydrophobic, non-polar, or only slightly polar polymeric plastic substrates are made hydrophilic and more polar by dual plasma treatment, first with an oxygen-containing plasma gas, and then with a nitrogen-containing plasma gas. Metallic substrate materials for medical devices, and components therefor, are treated with aminosilane primers to affix fast-reacting amino groups on the metallic surfaces. The resulting activated plastic or metal devices are then coated with the biocompatible hydrophilic PU prepolymer intermediates of the present invention to instantaneously affix the permanently bonded hydrophilic PU/PUR reactive base coats onto the substrate surfaces. Thereafter, a dissimilar hydrogel polymer, namely, a poly(N-vinylpyrrolidone) hydrogel polymer is applied as a dilute aqueous solution to convert the highly hydrophilic PU/PUR prepolymer intermediate to a hydrogel polymer while simultaneously "commingling" the dissimilar polymers in a single step to form compatible, permanently "inter-twined" polymer networks (IPN's) and/or association complexes between the combinations of hydrogel species. These compositions are utilizable for medical devices, and satisfy all of the above requirements. In addition to the slippery coating compositions themselves, the present invention also encompasses slippery materials composed of polymeric plastic or rubber, or metal substrates coated with the slippery coating compositions, and products fabricated from the slippery materials, including, especially, slippery coated medical devices such as catheters, catheter balloons and stents. The coated devices of the present invention are particularly well-suited for use as angioplasty devices, exhibit slipperiness and remarkable tenacity of adherence to the substrate and unusual wear performance properties during use when they are manipulated and dynamically acted upon in the presence of blood.

The present invention encompasses cohesive biocompatible slippery polyurethane-polyurea (PU/PUR) hydrogel coatings which are covalently bonded to and which tenaciously adhere to plasma-treated polymeric plastic or rubber substrates, or chemically-treated metallic substrates, and which further contain at least one additional hydrogel polymer, having a dissimilar composition to the PU/PUR hydrogel, to form a commingled hydrogel network. This combination, involving the use of at least two different hydrogel polymers, results in unexpected improvements with respect to the lubricity and permanence of the coatings. The coating compositions of the present invention are covalently bonded, tenaciously adhering, cohesive, biocompatible, slippery PU/PUR hydrogels in combination with at least one additional, compositionally different, hydrogel polymer, which results in synergism with respect to slipperiness and wear of the coatings brought about by the use of the at least two compatible hydrogel systems which are "commingled" with each other.

The present invention still further encompasses methods for the formation of such coatings and for the application of such coatings to polymeric substrates and metal substrates. In the case of polymeric substrates, generally, the method involves the steps of first plasma-treating plastic polymer substrates and affixing highly reactive amino groups onto their surfaces; next applying a biocompatible hydrophilic polyurethane NCO-terminated prepolymer adduct intermediate to the substrate to form and permanently affix the resulting covalently bonded hydrophilic PU/PUR "prepolymer intermediate" on the organic polymer substrate. The covalently attached PU/PUR boundary layer is next converted to a "commingled" hydrogel network coating by exposing it to an aqueous solution of the dissimilar hydrogel polymer (e.g. a poly(N-vinylpyrrolidone) hydrophilic polymer), in the presence of a catalytic quantity of accelerators. The formation of the commingled hydrogels can be conducted in the presence of fast reacting polyamine chain extenders and/or catalysts.

The covalently attached protective PU/PUR hydrogel coating and its combination with the structurally dissimilar, poly(N-vinylpyrrolidone) hydrogel polymer is slippery when wet and the simultaneously formed "commingled" dual layer surface exhibits excellent permanence when exposed to dynamic forces in the presence of various body fluids, especially blood. Furthermore, these coatings, being derived from materials exhibiting essentially no toxic behavior in their hydrogel state, greatly enhance the biocompatibility of the resulting medical device during use and exhibit excellent adhesion to the plasma-treated substrate surfaces.

It is known that surface treatment of polymeric surfaces by way of radio frequency plasma discharge conditions can activate the polymeric surfaces with respect to the physical and chemical characteristics of the boundary layers. It has also been discovered that metallic surfaces can be primed efficiently for the attachment of the hydrophilic PU/PUR prepolymer adduct intermediates by means of organic aminosilanes exhibiting NCO-reactive primary or secondary amine moieties. It is further known that various surface coatings of medical devices can enhance lubricity and biocompatibility of the medical apparatus when in contact with body fluids. In order to obtain excellent adhesion, good strength, permanence, and biocompatibility of the barrier coats, their physical and chemical characteristics are immensely important. To affix barrier coats to various surfaces the use of polyurethane polymers and/or reactive isocyanate intermediates have often been suggested. It is well known that the isocyanate derivatives from aromatic polyisocyanates exhibit much greater reactivity or other interactions with substrate boundary layers, for example due to surface moisture or substrate polarity, than do the slower reacting araliphatic, cycloaliphatic or heterocyclic isocyanates containing NCO groups that exhibit often not only appreciably lower rate of reaction but oftentimes also significant steric hindrance with regard to chemical interaction with active hydrogen compounds. There is evidence, however, that aromatic-based polyurethanes can hydrolyze or biodegrade to yield aromatic amine contaminants, many of which are carcinogens or suspected carcinogens. Therefore, unless this situation can be avoided, it may be inadvisable to employ the aromatic isocyanates in slippery barrier coatings for subsequent use in the blood stream since the mechanical action asserted upon the medical apparatus can inadvertently break away a portion of the coating during manipulation inside the blood vessels. The isocyanate-derived hydrogels of the present invention include those derived from aliphatic, cycloaliphatic, araliphatic, aromatic and heterocyclic types of polyisocyanate prepolymer adduct intermediates. The preferred isocyanate hydrogels include all of the aforementioned except those derived from aromatic polyisocyanate prepolymer adduct intermediates, because of the potential toxic effects of the latter. Most of the preferred isocyanate hydrogels are known to yield hydrophilic urethane/urea polymers and degradation products possessing good biocompatibility and very low order of toxicity. A predominant number of the preferred polyisocyanates, however, contain NCO groups which exhibit much lower order of activity than the aromatic isocyanates. Consequently, it is necessary to change the chemical nature of the substrate surfaces in a manner to obtain practically immediate cohesive bonding of the boundary coatings to said polymer substrates to accomplish suitable methods of manufacture of such medical apparatus.

The present invention also encompasses a process for rendering polymeric materials which are intrinsically non-polar and hydrophobic, polar and hydrophilic, in order that they are made receptive to being coated with the commingled hydrogels of the present invention.

The present invention also includes a process for the surface treatment of hydrophobic, non-polar or only slightly polar polymers in order to render their surface, more polar and hydrophilic so that the durable, tenaciously adhering, slippery, commingled hydrogel coatings of a hydrophilic polyurethane-polyurea (PU/PUR) hydrogel polymer and a poly(N-vinylpyrrolidone) hydrogel polymer may subsequently be applied to the polymer surface, especially for use in medical devices intended for insertion into a patient, and which, accordingly, come into contact with various body fluids, especially blood. The hydrophilicization process of the present invention includes one embodiment in which the non-polar hydrophobic polymeric substrate material is rendered polar and hydrophilic through a first oxidative chemical treatment step, followed by a plasma treatment step; a second embodiment of the process in which a two-step dual-plasma treatment of the substrate is performed; and still another embodiment of the process wherein the initial plasma treatment with one or more plasma gases is followed by application of a gas post-stream without plasma, which can also introduce functional groups onto the substrate surface depending on the composition of the post-stream.

It has been demonstrated that the affixation of amino groups to the substrate can be accomplished by plasma treatment of the medical device by means of ammonia, organic amines, optionally nitrous oxide (amino plus hydroxyl groups), or nitrogen as the plasma gases, or mixtures of these gases. Amino groups can bring about instantaneous reaction of the substrate surface with any of the isocyanate derivatives contemplated in the present invention. However, the amino groups are particularly useful with respect to the rather sluggish isocyanate species that are attached to secondary or tertiary carbon atoms of many polyisocyanates contemplated for the manufacture of the hydrophilic PU prepolymer intermediates utilized in the invention. We have discovered that in the case of highly hydrophobic plastic substrates, for example, various polyethylenes, it is extremely useful to modify the hydrophobic surface, to make it more hydrophilic, first, by means of oxidative chemical or oxygen-containing plasma treatments, optionally in the presence of argon (AR) gas, followed by exposure to nitrogen-containing plasma gases; or alternatively, with gaseous ammonia without plasma, after first treating the hydrophobic substrates with oxygen-containing plasma gases, optionally in the further presence of Ar, to affix reactive amino groups onto the substrate surface. Various combinations of these treatments can be utilized. After plasma exposure, a coating solution having between about 1% to about 20% solids, preferably between 2% to 6% solids, of an isocyanate-terminated hydrophilic prepolymer intermediate adduct derived from water-soluble hydrophilic polyether polyols and polyisocyanates selected from the group consisting of aliphatic, cycloaliphatic, araliphatic, aromatic, and heterocyclic polyisocyanates, is applied to the treated substrate surface, where it immediately forms the covalently bonded PU/PUR prepolymer, allowed to dry, and the coatings are then converted to protective lubricious hydrogel layers upon the devices' surface by exposure to a dilute aqueous solution containing one or more additional structurally dissimilar hydrogel polymers. If desired, the hydrogel formation of the PU/PUR hydrogel can be catalyzed by procedures known in the art. Highly preferred hydrophilic PU/PUR prepolymer adduct intermediates of the present invention are the adducts of isophorone diisocyanate (IPDI), as well as the adducts of isomer mixtures of methylene bis(4-cyclohexylene)diisocyanates (DESMODUR W; MILES CORP.).

In a preferred embodiment, the protective slippery compound comprises a hydrophilic PU/PUR prepolymer intermediate derived from a copolyether polyol of ethylene and/or propylene oxides, and an isocyanate containing aliphatically bound NCO groups to optimize biocompatibility, since corresponding polyamines resulting from hydrolysis or biodegradation of such polyurethanes are in general biocompatible. Random copolyethers facilitate handling of the prepolymer intermediates since the preferred types are liquids at room temperature thus providing easier handling characteristics in commercial practice. The preferred plasma gases are ammonia or mixtures of ammonia with organic amines to optimize formation of amino groups on the substrate surface. The hydrogel formation can be conducted without a catalyst, or in the presence of catalysts such as inorganic bases, low boiling tertiary amines, or preferably primary or secondary amines that become part of the hydrogel polymer. These catalysts are readily soluble in the aqueous phase of the at least one dissimilar hydrogel polymer which is a water-soluble polysaccharide(s), a water-soluble salt thereof, or is a water-soluble poly(1,2-oxyalkylene) homopolymer(s), such as a polyethyleneoxide polymer.

The coatings and the methods of the present invention are particularly well suited for affixing tenaciously adhering coatings of slippery, wet hydrogels, as well as dried coatings thereof, to substrates such polyethylene, terephthalate, block copolymers comprising aliphatic polyethers and aromatic polyesters, block copolymers from aliphatic polyethers and polyamides, polyamides, polyimides, polyurethanes, or hydrocarbon polymers such as polyethylene and polypropylene, synthetic hydrocarbon elastomers such as butadiene/styrene copolymers, block copolymers of butadiene and styrene, ethylene/propylene copolymers, other synthetic rubbers such as nitrile rubbers or ethylene/alkyl acrylate copolymers, as well as natural rubber. It is also feasible to affix the tenaciously adhering, slippery, wet hydrogel coatings, and dried versions thereof, of the present invention, to aminosilane-treated metal surfaces. Many of these substrates find use in medical devices such as various types of catheters, and catheter devices for coronary angioplasty, including balloons.

It has been discovered that commingled hydrogel coatings wherein a polyurethane-polyurea hydrogel polymer is commingled with a poly(N-vinylpyrrolidone) hydrogel polymer surprisingly exhibit particularly good wear performance on medical devices which come into contact with body fluids, especially blood.

The compositions and methods of the present invention designed to covalently attach hydrophilic PU/PUR hydrogel coatings "commingled" with at a poly(N-vinylpyrrolidone) hydrogel polymer, to plasma-treated plastic surfaces or aminosilane-treated metallic substrates, are particularly useful for the manufacture of medical devices such as catheters, balloon catheters, and the like which have coated surfaces that are vastly superior for use in blood in comparison with silicone coatings and/or other hydrophilic coatings previously commonly used in coronary angioplasty. The wear performance upon dynamic exposure in blood is normally lost rather quickly by the coated medical devices of the prior art. In contract thereto, the covalently bonded PU/PUR hydrogel coatings of the present invention, "commingled" with a poly(N-vinylpyrrolidone) hydrogel polymer, and affixed to various medical apparatus in accordance with the methods set forth in the present invention, for example, diagnostic catheters, balloon catheters comprising PET, HYTREL, PU, nylons, polyolefins, polyimides, and other polymers have exhibited very unusual durability even after many test cycles when exposed to dynamic forces in blood. These surprising observations and results represent a decided advance of the art of slippery coatings for medical devices.

DETAILED DESCRIPTION OF THE INVENTION

The tenaciously adhering, slippery coating compositions of the present invention are particularly suitable for medical devices, including catheters, balloons for use in conjunction with catheters, guidewires, metal tubing, and other devices having operational requirements and properties that can be improved by attaching lubricious coatings to one or more surfaces of such devices which come in contact with body fluids. In accordance with the invention, the coatings include hydrophilic PU/PUR "prepolymer intermediates" which are cohesively attached to the organic plastic or rubber polymer substrates or metal substrates from which the medical devices or components thereof are fabricated, and upon exposure thereof to the aqueous solution of one or more dissimilar hydrogel polymers which are water-soluble polysaccharides, water-soluble salts thereof, or water-soluble polyoxyethylenes, cause the resulting "commingled" hydrogels or "association polymer" coatings to form lubricating films on the apparatus or functional components thereof. The slippery coatings are characterized by good biocompatibility and good permanence of adhesion when exposed to dynamic forces in typical body fluids, such as blood and other chemically and physiologically complex fluid compositions.

The present invention also relates to a method for the production of coated medical devices by means of first exposing an uncoated polymeric device or precursor for subsequent fabrication into a device, or a parison for subsequent blow-molding into a balloon for use in conjunction with a medical device, to a high frequency plasma with microwaves, or alternatively to a high frequency plasma combined with magnetic field support, or chemically treating a metallic device, to yield the desired reactive surfaces bearing at least a substantial portion of reactant amino groups upon the substrate to be coated, which groups can combine instantly with the terminal isocyanate groups of the prepolymer intermediates deposited upon the reactively coated polymer or metal substrate surfaces. Particularly useful starting prepolymer intermediates for coating onto the polymer or metal substrate surfaces according to the present invention include hydrophilic polyurethane prepolymer intermediates derived from water-soluble polyether polyols and organic polyisocyanates. With respect to desired biocompatibility, preferred polyisocyanates comprise aliphatic, cycloaliphatic, araliphatic, and heterocyclic polyisocyanates containing aliphatically attached terminal isocyanate groups. On account of the relatively slow reactivity of the isocyanate groups of this class, the plasma treatment of polymeric substrates or chemical treatment of metal substrates is conducted in a manner to yield rapidly reacting amino groups as the major desirable active species that is present on the boundary layer of the substrates. Therefore, the plasma treatment is carried out with plasma gases containing nitrogen atoms. In the case of very hydrophobic polymer substrates such as various polyethylenes, it has been found desirable to conduct initial surface treatments which render the surface hydrophilic and then follow up with various consecutive treatments to affix very reactive functional groups onto the substrates. Particularly desirable highly reactive chemical functional groups include primary and secondary amino groups which readily react at room temperature with the relatively slow reacting NCO groups of the preferred polyisocyanates and the hydrophilic PU prepolymers thereof preferentially employed as coating intermediates in the present invention. The first substrate treatment step usually comprises of a chemical oxidation treatment, or alternatively, one or more plasma-gas exposures to oxygen-containing gases, optionally in the presence of argon (Ar) gas to generate free radicals, and the consecutive step is carried out with plasma gases containing nitrogen atoms, or alternatively, in certain embodiments of the invention, in the form of application of gaseous post-streams containing ammonia and/or organic amine-containing gases which react with the treated surface immediately after a first-step plasma treatment with oxygen-containing gases, or oxygen/argon plasma gas combinations. As mentioned, this consecutive step can also be performed with plasma gases such as ammonia, volatile organic amines, or mixtures thereof. The net result is the achievement of a substrate surface which is hydrophilic, and contains also a significant number of primary and/or secondary amino groups which can react readily with the relatively sluggish NCO groups of the PU prepolymers used in accordance with the present invention. In the case of metallic components such as guidewires or metal tubes made from substrates such as stainless steel or titanium, or metal alloys of steel, nickel, titanium, molybdenum, cobalt, and chromium, or other metals, such as the alloys nitinol (nickel-titanium alloy) and vitallium (cobalt-chromium alloy), amino groups are attached to the metal substrate surfaces by means of organic aminosilane primer treatments.

Quite surprisingly, the surface geometry of polymeric materials used for the manufacture of medical apparatus remains relatively unaffected by plasma treatment. Furthermore, it has been established that if the plasma treatment parameters are followed carefully, the degree of amino group fixation on the surface is such that the isocyanate-containing coating intermediates which are deposited thereon do not crosslink prematurely before the hydrogel formation step is undertaken. These factors are of importance because it is believed that the slipperiness efficiency of the hydrophilic hydrogel is substantially improved by conducting the polymer formation reaction in such manner as to form hydrophilic polymer chains of substantial length and limited degree of crosslinking to optimize the mobility of the relatively elastic resultant molecular structure of the coating surfaces on which it is desired to achieve low coefficients of friction. Premature crosslinking or excessive crosslinking of the coatings surfaces is believed to be detrimental to achieving improved slipperiness due to maintaining low coefficient of friction, lowering of dynamic drag forces, and preservation of high elasticity which is known to improve frictional wear.

Typical polymeric substrates often employed for the medical devices of the present invention include thermoplastic polyurethanes (TPU), polyesters such as polyethylene terephthalate (PET), nylon polymers such as nylon-11 and nylon-12, block copolymers of polyether and polyester polymers (for example various HYTREL® block copolymers, available from DuPONT), block copolymers of polyether polymers and polyamides (for example, PEBAX® resin series, available from ATOCHEM), polyimides, polyolefins such as polyethylenes (PE) and polypropylenes (PP), synthetic rubbers, including SBR and EPDM, thermoplastic hydrocarbon polymers (KRATON®, available from SHELL, and other similar commercial products from other sources), as well as natural rubber. For catheter applications used in angioplasty, components made from TPU, PET, nylons 11 and 12, HYTREL, PEBAX, and PE are preferred polymeric substrates. For catheter balloons used in coronary angioplasty preferred polymeric substrates are PET, nylons and PE.

It is often advantageous to pretreat the polymeric substrate surface before plasma treatment with polar or nonpolar solvents for a period of from about 15 seconds, or less, to longer than several minutes, in order to remove any surface impurities such as lubricants, antioxidants, plasticization agents, release agents, and the like. These impurities can originate from initial polymer manufacturing processes or from plastics forming techniques such as extrusion, injection-molding, blow-molding, and the like. Typical solvents which can be used for this purpose include alcohols such as methanol, ethanol, isopropanol, and the like; ketones such as acetone, methylethyl ketone, and the like; chlorinated hydrocarbons such as methylene chloride, 1,1,1-trichloroethane, and the like; hydrocarbons such as pentanes, n-hexane, petroleum ethers, other cleaning spirits, and the like; ethers such as diisopropyl ether, dioxane, tetrahydrofuran, and the like; and mixtures of the above. In the case of non-flammable cleaning solvents the removal of surface impurities can be carried out by means of vapor degreasers, a procedure well known in the art. It is also within the scope of the present invention to utilize aqueous solutions of nonionic, anionic, and cationic surfactants as washing fluids, if desired, followed by rinsing with water or distilled water to remove surface impurities that can interfere with the plasma treatment. Impurities on the substrate surface which are not part of the polymer matrix can detract from the formation of direct cohesive bonds with the substrates. Likewise, metal substrates should be degreased with organic solvents, or washed with appropriate detergents or roughened mechanically, or treated with combinations of the above procedures, before the application of organosilane, especially aminosilane, primers.

The speed of formation of cohesive bonds upon the substrate surfaces depends on the reactivity of the functional groups attached to a polymeric substrate surface by means of plasma treatment or to a metallic substrate surface by means of chemical treatment, as well as upon the rate of reaction of the terminal isocyanate groups that are present in the intermediate polymer coating affixed to the substrates. Fast reacting NCO groups that are attached directly to the aromatic ring structure can be made to form cohesive bonds with a variety of relatively slower reacting functional groups which are present in the base plastic or rubber of a polymer substrate, on the chemically- or plasma-treated surface of a polymer substrate, or on the chemically-treated surface of a metal substrate. In most cases, aromatic isocyanates and their derivatives can form cohesive bonds at from room temperature to somewhat elevated temperatures (around 70° C.) with reactive chemical functional groups such as hydroxyl, urethane, urea, amide, carboxyl, carbonyl, and others that are either originally present on a non-metal substrate, or which have been affixed to a polymeric plastic or rubber substrate by oxidative- or plasma-treatment, or by other means, to yield, for example, hydroxyl or carboxyl groups; or which have been affixed to a metallic substrate surface by the chemical treatment thereof. To facilitate such reactions after evaporation of the solvents present in the intermediate prepolymer coatings solution, the coated substrate can be heated to from 40° C. up to about 70° C., or higher, to effect formation of cohesive bonds with slower reacting chemical functional groups such as urethane, urea, amide, carboxyl, and even hydroxyl groups that are either present in the initial substrate polymer, or have been affixed to the polymer substrate by exposure to plasma treatment in the presence of various plasma gases. Oftentimes non-plasma treated plastic surfaces having NCO-reactant functional components as part of their polymer make-up, or having oxidized surfaces, or even surface moisture, can result in reasonably good adhesion when exposed to aromatic polyisocyanates or derivatives therefrom. However, these procedures give only borderline or inadequate results in the presence of most commercially available aliphatic, particularly cycloaliphatic, and sterically hindered araliphatic diisocyanates and their derivatives which contain much slower reacting isocyanate groups. Furthermore, from the standpoint of toxicity and/or biocompatibility of polyurethanes derived from aromatic polyisocyanates and their hydrolytic or biodegraded aromatic polyamine by-products, they are less desirable when used in anatomical contact because aromatic amines are potentially hazardous carcinogens. In this respect, caution must be exercised when the outer coatings on medical devices are employed in intravenous application in direct contact with body fluids, for example, in blood. Certain aromatic polyisocyanates have, however, been previously shown to be biocompatible. The use of aliphatic, cycloaliphatic, araliphatic, and heterocyclic polyisocyanates and prepolymers thereof containing only aliphatically-bound terminal NCO groups is, however, much preferred because of the appreciably lower risk with respect to toxicity of their PU polymers and in particular because of the known good biocompatibility of their polyamine degradation products.

However, on account of the considerably slower reactivity of the above mentioned aliphatically-bound, and oftentimes also sterically hindered, terminal isocyanate groups attached to the diisocyanates and derivatives thereof comprising the preferred embodiments of the present invention, it has been found advisable to plasma- or chemically- treat the polymeric and/or metal substrates used for the various medical devices encompassed by the present invention. Plasma and/or chemical treatment must be designed to affix primary and/or secondary amino groups preferentially or at least partially, upon the surfaces of the polymer or metal substrates. The amino groups react instantly with the isocyanate groups of the prepolymer coatings intermediates, even before the coatings solvents are evaporated. Hence, the plasma treatment must be conducted in the presence of plasma gases that yield amino groups as at least a substantial portion of the functional groups affixed to the substrate surface. Plasma gases that can yield amino functionality must contain nitrogen as part of their chemical composition. Therefore, the plasma treatment is preferably carried out with plasma gases containing nitrogen atoms, such as ammonia, primary and secondary amines, nitrous oxide, nitrogen, other gases containing nitrogen moieties, and mixtures of such gaseous compounds. Ammonia and low molecular weight organic amines as well as mixtures thereof, being in the vapor state at relatively low temperatures, are preferred plasma gases. In the case of treatment of very hydrophobic substrate surfaces, such as various polyethylenes (PE), rather hydrophobic polymers such as nylons 11 and 12, and even synthetic hydrocarbon elastomers, or natural rubber, it is advantageous to render the substrate surface hydrophilic or more hydrophilic before the affixation of very reaction functional groups, such as primary and secondary amino groups, and the like, which exhibit high reactivity with the hydrophilic PU/PUR prepolymers of the present invention.

It is known that surface treatment of polymeric surfaces by way of radio frequency plasma discharge conditions can activate the polymeric surfaces with respect to the physical and chemical characteristics of the boundary layers. It has also been discovered that metallic surfaces can be primed efficiently for the attachment of the hydrophilic PU/UR prepolymer adduct intermediates by means of organic aminosilanes exhibiting NCO-reactive primary or secondary amine moieties. It is further known that various surface coatings of medical devices can enhance lubricity and biocompatibility of the medical apparatus when in contact with body fluids. In order to obtain excellent adhesion, good strength, permanence, and biocompatibility of the barrier coats, their physical and chemical characteristics are immensely important. To affix barrier coats to various surfaces the use of polyurethane polymers and/or reactive isocyanate intermediates have often been suggested. It is well known that the isocyanate derivatives from aromatic polyisocyanates exhibit much greater reactivity or other interactions with substrate boundary layers, for example due to surface moisture or substrate polarity, than do the slower reacting aliphatic, araliphatic, cycloaliphatic and heterocyclic isocyanates containing NCO groups that exhibit often not only appreciably lower rate of reaction but oftentimes also significant steric hindrance with regard to chemical interaction with active hydrogen compounds. There is evidence that aromatic-based polyurethanes can hydrolyze or biodegrade to yield aromatic amine contaminants, many of which are carcinogens or suspected carcinogens. Therefore, unless this situation can be avoided, it may be inadvisable to employ the aromatic isocyanates in slippery barrier coatings for subsequent use in the blood stream since the mechanical action asserted upon the medical apparatus can inadvertently break away a portion of the coating during manipulation inside the blood vessels. The isocyanate-derived hydrogels of the present invention include those derived from aliphatic, cycloaliphatic, araliphatic, aromatic and heterocyclic types of polyisocyanate prepolymer adduct intermediates. The preferred isocyanate hydrogels include all of the aforementioned except those derived from aromatic polyisocyanate prepolymer intermediates, because of the potential toxic effects of the latter. Most of the preferred isocyanate hydrogels are known to yield hydrophilic urethane/urea polymers and degradation products possessing good biocompatibility and very low order of toxicity. A predominant number of the preferred polyisocyanates, however, contain NCO groups which exhibit much lower order of activity than the aromatic isocyanates. Consequently, it is necessary to change the chemical nature of the substrate surfaces in a manner to obtain practically immediate cohesive bonding of the boundary coatings to said polymer substrates to accomplish suitable methods of manufacture of such medical apparatus.

It has been demonstrated that the affixation of amino groups to the substrate can be accomplished by plasma treatment of the medical device by means of ammonia, organic amines, optionally nitrous oxide (amino plus hydroxyl groups), or nitrogen as the plasma gases, or mixtures of these gases. Amino groups can bring about instantaneous reaction of the substrate surface with any of the isocyanate derivatives contemplated in the present invention. However, the amino groups are particularly useful with respect to the rather sluggish isocyanate species that are attached to secondary or tertiary carbon atoms of many polyisocyanates contemplated for the manufacture of the hydrophilic PU/UR prepolymer adduct intermediates utilized in the invention. We have discovered that in the case of highly hydrophobic plastic substrates, for example various polyethylenes, it is extremely useful to first modify the hydrophobic surface to make it more hydrophilic by means of oxidative chemical or oxygen-containing plasma treatments, optionally in the presence of argon (Ar) plasma gas, followed by nitrogen-containing plasma gases, or alternatively with a gaseous post-stream of ammonia without plasma, after first treating the hydrophobic substrates with oxygen-containing plasma gases, optionally in the presence of Ar, to affix reactive amino groups onto the substrate surface by various combination of such treatments. After plasma exposure, a coating solution having between about 1% to about 20% solids, preferably between 2% to 6% solids, of an isocyanate-terminated hydrophilic prepolymer intermediate adduct derived from water-soluble hydrophilic polyether polyols and polyisocyanates selected from the group consisting of aliphatic, cycloaliphatic, araliphatic, aromatic, and heterocyclic polyisocyanates, is applied to the treated substrate surface, where it immediately forms the covalently bonded PU/UR prepolymer, allowed to dry, and the coatings are then converted to protective lubricious hydrogel layers upon the devices' surface by exposure to a dilute aqueous solution containing one or more additional structurally dissimilar hydrogel polymers. If desired, the hydrogel formation of the commingled PU/PUR hydrogel can be catalyzed by procedures known in the art. Highly preferred hydrophilic PU/UR prepolymer intermediates of the present invention are the adducts of isophorone diisocyanate (IPDI), as well as the adducts of isomer mixtures of methylene bis(4-cyclohexylene)diisocyanates (DESMODUR W; MILES CORP.).

In a preferred embodiment, the protective slippery compound comprises hydrophilic PU/UR prepolymer intermediates derived from copolyether polyols of ethylene and/or propylene oxides, and isocyanates containing aliphatically bound NCO groups to optimize biocompatibility, since corresponding polyamines resulting from hydrolysis or biodegradation of such polyurethanes are in general biocompatible. Random copolyethers facilitate handling of the prepolymer adduct intermediates since the preferred types are liquids at room temperature thus providing easier handling characteristics in commercial practice. The preferred plasma gases are ammonia or mixtures of ammonia with organic amines to optimize formation of amino groups on the substrate surface. The hydrogel formation can be conducted without a catalyst, or in the presence of catalysts such as inorganic bases, low boiling tertiary amines, or preferably primary or secondary amines that become part of the hydrogel polymer. These catalysts are readily soluble in the aqueous phase of the at least one dissimilar hydrogel polymer which is a water-soluble polysaccharide(s), a water-soluble salt thereof, or is a water-soluble poly(1,2-oxyalkylene) homopolymers, such as a polyethyleneoxide polymers, or a PVP polymer.

The coatings and the methods are particularly well suited to affix lubricious coatings to substrates such as polyethylene terephthalate, block copolymers comprising aliphatic polyethers and aromatic polyesters, block copolymers from aliphatic polyethers and polyamides, polyamides, polyimides, polyurethanes, or hydrocarbon polymers such as polyethylene and polypropylene synthetic hydrocarbon elastomers, as well as natural rubber. It is also feasible to affix the tenaciously adhering, slippery hydrogel coatings of the present invention to aminosilane-treated metal surfaces. Many of these substrates find use in medical devices such as various types of catheters, and catheter devices for coronary angioplasty, including balloons.

Typical polysaccharides and/or salts thereof which are useful for the formation of lubricious polymers comprising combinations of PU/PUR hydrogels and polysaccharide hydrogels include, by way of example, polysaccharides such as alginic acids and their alkali metal salts, said alginic acids consisting of various copolymer segments of D-mannuronic acid and L-glucuronic acid, depending upon their natural origin. Other naturally occurring water-soluble seaweed gums suitable for this use are the carrageenan types, which comprise linear polysaccharides of alternating 1,3-linked β-D-galactopyranosyl and 1,4-linked α-D-galactopyranosyl units. Due to their half-ester sulfate groups the carrageenans are anionic polyelectrolytes, and their sodium salts form water-soluble stable hydrogels which can be readily incorporated as the hydrogel combinations depicted by the present invention. Other suitable polysaccharide hydrogels comprise hyaluronic acids and their alkali metal salts, chondroitin sulfates and the corresponding alkali metal sulfates and carboxylates represent further useful water-soluble hydrogel polymers as components of the present invention. Typical water-soluble derivatives from celluloses that are suitable as hydrogel polymers of the instant invention comprise water-soluble sodium carboxymethyl celluloses, as well as water-soluble hydroxyethyl celluloses or hydroxypropyl celluloses, and the like, all well known in the art. Most of these materials exhibit a very low order of toxicity and are usually biocompatible. Further water-soluble polymers useful as hydrogel polymer ingredients of the present invention are poly(oxyethylene) homopolymers having molecular weights of from about 100,000 or lower, to about 5,000,000 or higher, which are known as POLYOX® polymers (UNION CARBIDE). Additional typical water-soluble polymers useful as dissimilar hydrogel polymers of the present invention include poly(N-vinylpyrrolidones) having molecular weights of from about 10,000 to about 340,000 (such as the PVP polymers available from GAF Corp.).

The compositions and methods of the present invention designed to covalently attach hydrophilic PU/PUR hydrogel coatings "commingled" with at least a second dissimilar hydrogel polymer as defined by the present invention, to plasma-treated plastic surfaces or aminosilane-treated metallic substrates, are particularly useful for the manufacture of medical devices such as catheters, balloon catheters, and the like which have coated surfaces that are vastly superior for use in blood in comparison with silicone coatings and/or other hydrophilic coatings previously commonly used in coronary angioplasty. The wear performance upon dynamic exposure in blood is normally lost rather quickly by the coated medical devices of the prior art. In contrast thereto, the covalently bonded PU/PUR hydrogel coatings of the present invention, "commingled" with at least one dissimilar hydrogel polymer described herein, and affixed to various medical apparatus in accordance with the methods set forth in the present invention, for example, diagnostic catheters, balloon catheters comprising PET, HYTREL, PU, nylons, polyolefins, polyimides, and other polymers have exhibited very unusual durability even after many test cycles when exposed to dynamic forces in blood. These surprising observations and results represent a decided advance of the art of lubricious coatings for medical devices.

DETAILED DESCRIPTION OF THE INVENTION

The tenaciously adhering, slippery coating compositions of the present invention are particularly suitable for medical devices, including catheters, balloons for use in conjunction with catheters, guidewires, metal tubing, and other devices having operational requirements and properties that can be improved by attaching lubricious coatings to one or more surfaces of such devices which come in contact with body fluids. In accordance with the invention, the coatings include hydrophilic PU/UR "prepolymer intermediates" which are cohesively attached to the organic plastic or rubber polymer substrates or metal substrates from which the medical devices or components thereof are fabricated, and upon exposure thereof to the aqueous solution of one or more dissimilar hydrogel polymers which are water-soluble polysaccharides, water-soluble salts thereof, water-soluble polyoxyethylenes, or water-soluble PVP polymers cause the resulting "commingled" hydrogels or "association polymer" hydrogel coatings to form lubricating films on the apparatus or functional components thereof. The slippery coatings are characterized by good biocompatibility and good permanence of adhesion when exposed to dynamic forces in typical body fluids, such as blood and other chemically and physiologically complex fluid compositions.

The present invention also relates to a method for the production of coated medical devices by means of first exposing an uncoated polymeric device or precursor for subsequent fabrication into a device, or a parison for subsequent blow-molding into a balloon for use in conjunction with a medical device, to a high frequency plasma with microwaves, or alternatively to a high frequency plasma combined with magnetic field support, or chemically treating a metallic device, to yield the desired reactive surfaces bearing at least a substantial portion of reactant amino groups upon the substrate to be coated, which groups can combine instantly with the terminal isocyanate groups of the prepolymer intermediates deposited upon the reactively coated polymer or metal substrate surfaces. Particularly useful starting prepolymer intermediates for coating onto the polymer or metal substrate surfaces according to the present invention include hydrophilic polyurethane prepolymer intermediates derived from water-soluble polyether polyols and organic polyisocyanates. With respect to desired biocompatibility, preferred polyisocyanates comprise aliphatic, cycloaliphatic, araliphatic, and heterocyclic polyisocyanates containing aliphatically attached terminal isocyanate groups. On account of the relatively slow reactivity of the isocyanate groups of this class, the plasma treatment of polymeric substrates or chemical treatment of metal substrates is conducted in a manner to yield rapidly reacting amino groups as the major desirable active species that is present on the boundary layer of the substrates. Therefore, the plasma treatment is carried out with plasma gases containing nitrogen atoms. In the case of very hydrophobic polymer substrates, such as various polyethylenes, it has been found desirable to conduct initial surface treatments which render the surface hydrophilic and then follow up with various consecutive treatments to affix very reactive functional groups onto the substrates. Particularly desirable highly reactive functional groups include primary and secondary amino groups which readily react at room temperature with the relatively slow reacting NCO groups of the preferred polyisocyanates and the hydrophilic PU prepolymers thereof preferentially employed as coating intermediates in the present invention. The first substrate treatment step usually consists of a chemical oxidation treatment, or alteratively, one or more plasma-gas exposures to oxygen-containing gases, optionally in the presence of argon (Ar) gas to generate free radicals, and the consecutive step is carried out with plasma gases containing nitrogen atoms, or alternatively, in certain embodiments of the invention, by the application of gaseous post-streams containing ammonia and/or organic amine-containing gases which react with the treated surface immediately after a first-step plasma treatment with oxygen-containing gases, or oxygen/argon plasma gas combinations. As mentioned, this consecutive step can also be performed with plasma gases such as ammonia, volatile organic amines, or mixtures thereof. The net result is the achievement of a substrate surface which is hydrophilic and contains also a significant number of primary and/or secondary amino groups which can react readily with the relatively sluggish NCO groups of the PU prepolymers used in accordance with the present invention. In the case of metallic components such as guidewires or metal tubes made from substrates such as stainless steel or titanium, or metal alloys of steel, nickel, titanium, molybdenum, cobalt, and chromium, or other metals, such as the alloys nitinol (nickel-titanium alloy) and vitallium (cobalt-chromium alloy), amino groups are attached to the metal substrate surfaces by means of organic aminosilane primer treatments.

Quite surprisingly, the surface geometry of polymeric materials used for the manufacture of medical apparatus remains relatively unaffected by plasma treatment. Furthermore, it has been established that it the plasma treatment parameters are followed carefully, the degree of amino group fixation on the surface is such that the isocyanate-containing coating intermediates which are deposited thereon do not crosslink prematurely before the hydrogel formation step is undertaken. These factors are of importance because it is believed that the slipperiness efficiency of the hydrophilic hydrogel is substantially improved by conducting the polymer formation reaction in such manner as to form hydrophilic polymer chains of substantial length and limited degree of crosslinking to optimize the mobility of the relatively elastic resultant molecular structure of the coating surfaces on which it is desired to achieve low coefficients of friction. Premature crosslinking or excessive crosslinking of the coatings surfaces is believed to be detrimental to achieving improved slipperiness due to maintaining low coefficient of friction, lowering of dynamic drag forces, and preservation of high elasticity which is known to improve frictional wear.

Typical polymeric substrates often employed for the medical devices of the present invention include thermoplastic polyurethanes (TPU), polyesters such as polyethylene terephthalate (PET), nylon polymers such as nylon-11 and nylon-12, block copolymers of polyether and polyester polymers (for example various HYTREL® block copolymers, available from DuPONT), block copolymers of polyether polymers and polyamides (for example, PEBAX® resin series, available from ATOCHEM), polyimides, polyolefins such as polyethylenes (PE) and polypropylenes (PP), synthetic hydrocarbon polymers, such as SBR, EPDM, including thermoplastic hydrocarbon polymers (KRATON®, available from SHELL, and other similar commercial products from other sources), as well as natural rubber. For catheter applications used in angioplasty, components made from TPU, PET, nylons 11 and 12, HYTREL, PEBAX, and PE are preferred polymeric substrates. For catheter balloons used in coronary angioplasty preferred polymeric substrates are PET, nylons and PE.

It is often advantageous to pretreat the polymeric substrate surface before plasma treatment with organic solvents for a period of from about 15 seconds, or less, to longer than several minutes, in order to remove any surface impurities such as lubricants, antioxidants, plasticization agents, release agents, and the like. These impurities can originate from initial polymer manufacturing processes or from plastics forming techniques such as extrusion, injection-molding, blow-molding, and the like. Typical solvents which can be used for this purpose include alcohols such as methanol, ethanol, isopropanol, and the like; ketones such as acetone, methylethyl ketone, and the like; chlorinated hydrocarbons such as methylene chloride, 1,1,1-trichloroethane, and the like; hydrocarbons such as pentanes, n-hexane, petroleum ethers, other cleaning spirits, and the like; ethers such as diisopropyl ether, dioxane, tetrahydrofuran, and the like; and mixtures of the above. In the case of nonflammable cleaning solvents the removal of surface impurities can be carried out by means of vapor degreasers, a procedure well known in the art. It is also within the scope of the present invention to utilize aqueous solutions of nonionic, anionic, and cationic surfactants as washing fluids, if desired, followed by rinsing with water or distilled water to remove surface impurities that can interfere with the plasma treatment. Impurities on the substrate surface which are not part of the polymer matrix can detract from the formation of direct cohesive bonds with the substrates. Likewise, metal substrates should be degreased with organic solvents, or washed with appropriate detergents, or roughened mechanically, or treated with combinations of the above procedures before the application of organosilane, especially aminosilane, primers.

The speed of formation of cohesive bonds upon the substrate surfaces depends on the reactivity of the functional groups attached to a polymeric substrate surface by means of plasma treatment or to a metallic substrate surface by means of chemical treatment, as well as upon the rate of reaction of the terminal isocyanate groups that are present in the intermediate polymer coating affixed to the substrates. Fast reacting NCO groups that are attached directly to the aromatic ring structure can be made to form cohesive bonds with a variety of relatively slower reacting functional groups which are present in the base plastic or rubber of a polymer substrate, on the chemically- or plasma-treated surface of a polymer substrate, or on the chemically-treated surface of a metal substrate. In most cases, aromatic isocyanates and their derivatives can form cohesive bonds at from room temperature to somewhat elevated temperatures (around 70° C.) with functional groups such as hydroxyl, urethane, urea, amide, carboxyl, and others that are originally either present on a non-metallic substrate, or which have been affixed to a polymeric plastic or rubber substrate by oxidative- or plasma-treatment, or by other means, to yield, for example, hydroxyl or carboxyl groups; or which have been affixed to a metallic substrate surface by the chemical treatment thereof. To facilitate such reactions after evaporation of the solvents present in the intermediate prepolymer coatings solution, the coated substrate can be heated to from 40° C. up to about 70° C., or higher, to effect formation of cohesive bonds with slower reacting functional groups such as urethane, urea, amide, carboxyl, and even hydroxyl groups that are either present in the initial substrate polymer, or have been affixed to the polymer substrate by exposure to plasma treatment in the presence of various plasma gases. Oftentimes non-plasma treated plastic surfaces having NCO-reactant functional components as part of their polymer make-up, or having oxidized surfaces, or even surface moisture, can result in reasonably good adhesion when exposed to aromatic polyisocyanates or derivatives therefrom. However, these procedures give only borderline or inadequate results in the presence of most commercially available aliphatic, particularly cycloaliphatic and sterically hindered araliphatic, diisocyanates and their derivatives which contain much slower reacting isocyanate groups. Furthermore, from the standpoint of toxicity and/or biocompatibility, the use of polyurethanes derived from aromatic polyisocyanates and their hydrolytic or biodegradation aromatic polyamine by-products is less desirable in situations where the materials are in anatomical contact, because aromatic amines are potentially hazardous carcinogens. In this respect, caution must be exercised when the outer coatings on medical devices are employed in intravenous application in direct contact with body fluids, such as blood. Certain aromatic polyisocyanates have, however, been previously shown to be biocompatible. The use of aliphatic, cycloaliphatic, araliphatic, and heterocyclic polyisocyanates and prepolymers thereof containing only aliphatically-bound terminal NCO groups is, however, much preferred, because of the appreciably lower risk with respect to toxicity of their PU polymers, and in particular because of the known good biocompatability of their polyamine degradation products.

Because of the considerably slower reactivity of the above mentioned aliphatically-bound, and oftentimes also sterically hindered, terminal isocyanate groups attached to the diisocyanates and derivatives thereof comprising the preferred embodiments of the present invention, it has been found advisable to plasma-treat the polymeric or chemically- and/or metal substrates used for the various medical devices encompassed by the present invention. Plasma and/or chemical treatment must be designed to affix primary and/or secondary amino groups preferentially or at least partially, upon the surfaces of the polymer or metal substrates. The amino groups react instantly with the isocyanate groups of the prepolymer coatings intermediates, even before the coatings solvents are evaporated. Hence, the plasma treatment must be conducted in the presence of plasma gases that yield amino groups as at least a substantial portion of the functional groups affixed to the substrate surface. Plasma gases that can yield amino functionality must contain nitrogen as part of their chemical composition. Therefore, the plasma treatment is preferably carried out with plasma gases containing nitrogen atoms, such as ammonia, primary and secondary amines, nitrous oxide, nitrogen, other gases containing nitrogen moieties, and mixtures of such gaseous compounds. Ammonia and low molecular weight organic amines as well as mixtures thereof, being in the vapor state at relatively low temperatures, are preferred plasma gases. In the case of treatment of very hydrophobic substrate surfaces, such as various polyethylenes (PE), rather hydrophilic polymers such as nylons 11 and 12, and even synthetic hydrocarbon elastomers, or natural rubber, it is advantageous to render the substrate surface hydrophilic or more hydrophilic before the affixation of very reactive functional groups, such as primary and secondary amino groups, and the like, which exhibit high reactivity with the hydrophilic PU prepolymers of the present invention. There are several embodiments of the process for affixing amino groups to polyethylene substrates which we have discovered to be particularly useful in the present invention.

One embodiment of the process of the present invention for making hydrophobic plastic or rubber substrate materials hydrophilic and affixing highly reactive amino groups thereto, is a two-step procedure comprising first-treating the substrate material with a plasma gas containing oxygen, either pure, as air, water vapor, or mixtures thereof, followed by a second plasma treatment step with a nitrogen-containing gas, such as preferably ammonia, organic amines in the gaseous state, or mixtures thereof, to affix highly reactive primary or secondary amino groups onto the substrate. According to methods known in the art, the oxygen-containing plasma treatment step affixes the chemical groups consisting of hydroxyl groups, carbonyl groups, carboxyl groups, and mixtures thereof, thereby rendering the substrate more polar and hydrophilic; and the nitrogen-containing plasma gas step then affixes a substantial number of highly reactive amino groups onto the substrate. The unique combination of substrate hydrophilicity and amino functionality appears extremely well suited for covalently bonding the very hydrophilic PU prepolymer intermediates of the present invention to polyethylene substrates.

A second embodiment of the process of the present invention for making hydrophobic plastic or rubber substrate materials hydrophilic and for affixing highly reactive amino groups thereto, consists of a two-step procedure consisting of first chemically-treating the substrate material with oxidative reagents such as oxygen, ozone, peroxides, oxygen-fluorine ($O_2/F_2$) or air fluorine mixtures, peroxygen acids, and the like, all well known in the art, to render the substrate surface more polar and hydrophilic, and thereafter following the first step by a second step comprising the application of a nitrogen-containing plasma gas, for example preferably ammonia, organic amines in the gaseous state, or mixtures thereof to affix highly reactive primary or secondary amino groups onto the substrate. This combination of substrate hydrophilicity and amino functionality is also well suited for covalently bonding the very hydrophilic prepolymers of the present invention to various polyethylene substrates.

A third embodiment of the process of the present invention for making hydrophobic plastic or rubber substrate materials hydrophilic and affixing highly reactive amino groups thereto, consists of a two-step procedure comprising the application of a first-step treatment with a plasma gas to make the substrate more polar and hydrophilic while creating free radicals on the surface, for example, by means of non-reducing gases such as argon, or argon and ammonia, followed immediately by a second treatment step comprising the application of a gaseous non-plasma post-stream comprising preferably ammonia, organic amines in the gaseous state, or mixtures thereof, to affix highly reactive primary or secondary amino groups onto the substrate. Alternatively, the second non-plasma step can also be substituted by a plasma-treatment step whereby the nitrogen-containing gases are subjected to radio or microwave frequency plasma discharge. Again, the combination of substrate hydrophilicity and amino functionality are ideally suited for covalently bonding the very hydrophilic PU prepolymer intermediates of the present invention to various polyethylene substrates.

Hydrophobic plastic substrates which can be treated in accordance with the embodiments of the above processes include polyethylenes, nylons 11, and nylons 12. It is further within the scope of the present invention to subject medical devices, especially catheters, made from substrate materials composed of a mixture of chemically different polymers, for example, thermoplastic TPU products, polyamide-polyether block copolymers such as PEBAX® thermoplastic resins, polyimides, nylon 6 and nylon 6,6 and the like, to such treatments including the attachment of amino functionality onto the material of the substrate mixture, without interfering with the ability to affix the covalently bonded very hydrophilic PU prepolymers of the present invention to devices made from substrates containing diverse materials of construction.

Hydrophobic plastic substrates which can be exposed directly to a mixture of plasma gases comprising nitrogen-containing plasma gases, such as, for example, preferably ammonia, organic amines in the gaseous state, or mixtures thereof, to affix primary and secondary amino groups to the substrates, include homopolymers of propylene (PP), copolymers of ethylene and propylene (EP or EPDM elastomers), synthetic rubbers such as SBR, thermoplastic elastomers such as KRATON®, and natural rubber.

The above substrates can also be plasma-treated under conditions described in the art, for example, according to the conditions described in U.S. Pat. No. 5,112,736.

The resulting fairly polar and hydrophilic substrate surfaces are suitable for bonding the very hydrophilic prepolymer intermediates of the present invention thereto. In the case of the PP, EP, and EPDM plastics and rubbers, free radicals are generated on the tertiary carbons resulting from the polymerization of propylene; and in the case of the other hydrocarbon elastomers including synthetic and natural rubbers, the ionized ammonia or organic amine plasma combines with free radicals generated on their sites of unsaturation or at other locations.

Methods used for the application of consecutive plasma treatments to polyethylene (PE) substrates include first treating the substrate material with a plasma gas containing oxygen, either pure or in air, or a mixture of oxygen and one or more non-reducible gases, such as argon (Ar) and ammonia ($NH_3$), followed by a second treatment with either an ammonium-containing plasma gas consisting of ammonia low-boiling organic amines, or mixtures thereof, or with an ammonium-containing post-stream.

The inclusion of Ar in the first plasma treatment is desirable because its relatively heavy mass tends to cause the creation of additional free radicals on the surface, which facilitates further treatment in the second plasma treatment.

Generally, the hydrophobic substrates treated according to any of the above embodiments of the process of the present invention are non-polar and are made more polar by the treatment.

It is recommended that the substrate surface first be degreased with organic solvents or alternatively by washing with detergent solutions followed by rinsing with water and drying in order to clear, and prepare the substrate surface for the chemical or plasma treatment. After rendering the substrate surface more polar and hydrophilic in accordance with the various embodiments of the invention, the substrate is then exposed to a gaseous plasma containing nitrogen atoms. Preferred plasma gases include ammonia and/or organic amines, or mixtures thereof. Suitable organic amines are, by way of example, relatively low boiling primary and secondary amines having a structure $R_1NH_2$, $R_1NHR_2$, and $H_2N-R_3-NH_2$, wherein $R_1$ and $R_2$ are monovalent hydrocarbon radicals having from 1 to about 8 carbon atoms, preferably from 1 to 4 carbon atoms; and $R_3$ is a divalent hydrocarbon radical having from 2 to about 8 carbon atoms, preferably from 2 to about 6 carbon atoms.

Examples of suitable amines include methylamine, dimethylamine, ethylamine, diethylamine, ethylmethylamine, n-propylamine, allylamine, isopropylamine, n-butylamine, n-butylmethylamine, n-amylamine, n-hexylamine, 2-ethylhexylamine, ethylenediamine, 1,4-butanediamine, 1,6-hexanediamine, cyclohexylamine, n-methylcyclohexylamine, ethyleneimine, and the like.

Methods for plasma treatment with various plasma gases or combinations thereof are known in the art but generally lack the specificity demanded by the method employed in the present invention.

According to the present invention, for the case of ammonia and/or organic amines, or mixtures thereof as the plasma gases, a frequency in the radio frequency (RF) range, of from about 13.0 MHz to about 14.0 MHz, and preferably at about 13.56 MHz, with a generating power of from 0.1 Watts per square centimeter to about 0.5 Watts per square centimeter of surface area of the electrodes of the plasma apparatus is utilized. The plasma treatment comprises first evacuating the plasma reaction chamber to a desired base pressure of from about 10 to about 50 m Torr. After the chamber is stabilized to a desired working pressure, by flowing ammonia and/or organic amine gases, or mixtures thereof through the chamber at rates of from about 50 to about 730 standard ml per minute, typically from about 200 to 650 standard ml per minute, and a gas pressure of from about 0.01 to about 0.5 Torr, preferably from about 0.2 to about 0.4 Torr. A current having the desired frequency and level of power is supplied by means of electrodes from a suitable external power source. Power output is from 0 to about 500 Watts, preferably from about 100 to about 400 Watts. The temperature of the substrate is generally from about room temperature to about 50° C., and the treatment is usually carried out for a time of from about 30 seconds to about 10 minutes. The plasma chamber is initially at room temperature, however, during plasma treatment, the temperature in the chamber rises to a temperature not exceeding 60° C. due to molecular collisions. The plasma treatment can be performed by means of a continuous or batch process.

In the case of batch plasma treatment, the plasma surface treatment system known as PLASMA SCIENCE PS 0350 is utilizable (HIMONT/PLASMA SCIENCE, Foster City, Calif.). The system is equipped with a reactor chamber, an RF solid-state generator operating at 13.56 MHz capable of operating at from 0 to 500 watts power output, a microprocessor control system, and a complete vacuum pump package. The reaction chamber contains an unimpeded work volume of 16.75 inches in height, by 13.5 inches in width, by 17.5 inches in depth. For the application of the ammonia plasma and/or organic amine plasma, the equipment is operated at a power output of from about 50 to about 400 Watts, a gas flow rate of from about 400 to about 730 standard ml per minute for a time period of from 45 seconds, or less, up to about 6 minutes, and at temperatures of from room temperature to about 50° C. A preferred range is from about 60 to about 120 Watts and an ammonia and/or organic amine flow rate in the range of from about 700 to about 730 standard ml/min, under a vacuum from about 0.1 Torr to about 0.5 Torr, at a temperature of from about 30° C. to about 50° C., for a period of from about 15 seconds to about 3 minutes.

In order to define conditions for high permanence of adhesion of the hydrogel coatings, as well as the optimized degree of lubricity and permanence in blood, a highly preferred method of operation consists of operating at a power range of from about 100 to about 400 Watts, an ammonia flow rate of from about 200 to about 650 std ml/min, a vacuum of from about 0.1 Torr to about 0.5 Torr, a treatment temperature of from about 25° C. to about 40°

C., and an exposure time of from about 30 seconds to about 3 minutes. Optimization procedures for the plasma treatment and the performance of the covalently attached lubricious polyurethane hydrogel coatings can be determined on the basis of evaluation of dynamic drag forces versus exposure cycles and endurance in blood. Similar preferred conditions are utilized for nitrous oxide and nitrogen, or other gas mixtures containing nitrogen moieties as plasma gases.

A preferred set of conditions for dual-plasma treatment of a PE substrate is as follows:

For the first plasma treatment, a plasma gas stream composed of $O_2$ only or an $O_2/NH_3$ mixture or an $O_2/Ar$ mixture is used.

For an $O_2$ only gas stream, the gas pressure is from about 0.01 to about 0.09 Torr, preferably from about 0.05 to about 0.09 Torr, and the gas mass flow rate is from about 10 to about 100 standard ml per minute, preferably from about 80 to about 100 standard ml per minute.

For an $O_2/NH_3$ gas mixture, the gas pressure is from about 80 to about 90 m Torr for both the $O_2$ and $NH_3$. The $O_2:NH_3$ ratio is maintained at from about 0.5:1 to about 2:1, and preferably at about 1:1. The gas mass flow rate is from about 100 to about 200 standard ml per minute for $NH_3$ and from about 80 to about 100 standard ml per minute for $O_2$.

For an $O_2/Ar$ gas mixture, the gas pressure is from about 300 to about 400 m Torr for Ar and from about 65 to about 90 m Torr for $O_2$. The $O_2:Ar$ ratio is maintained at from about 0.1:1 to about 0.5:1, and preferably at about 0.25:1. The gas mass flow rate is from about 550 to about 650 standard ml per minute for Ar and from about 80 to about 100 standard ml per minute for $O_2$.

The plasma treatment time is about 2 minutes for all three plasma gas cases. For all three plasma gas cases, the base pressure is from about 10 to about 50 m Torr; output power is from about 0 to about 500 Watts, preferably from about 100 to about 400 Watts; and the chamber temperature varies from room temperature up to about 50° C. during treatment due to molecular collisions.

After the first plasma treatment with one of the above three plasma gases, the plasma chamber is again evacuated to a base pressure of from about 10 m Torr to about 30 m Torr, preferably about 20 m Torr. For the second plasma treatment, plasma treatment time is from about 30 seconds to about 5 minutes, preferably about 2 minutes; and output power is from about 100 Watts to about 300 Watts, preferably about 200 Watts. All other conditions including gas pressure, gas mass flow rate and chamber temperature are the same as for the single plasma treatment process using $NH_3$ gas, an organic amine gas, or a mixture thereof, as described above.

When a substrate surface is freshly plasmaed, especially by a heavy molecule such as Ar, the surface contains many free radicals. Post-stream treatment is one way to have more $NH_3$ molecules bond to the surface, thereby rendering the surface more hydrophilic.

For the dual plasma treatment process wherein the second treatment step is a post-stream treatment step, the preferable conditions are a treatment time of about 5 minutes; an output power of 0 Watts; a mass flow rate for $NH_3$ of from about 200 to about 650 standard ml per minute; and an $NH_3$ gas pressure of from about 0.2 to about 0.4 Torr.

Polymeric substrates which contain auxiliary chemicals such as antioxidants, ultraviolet and other light stabilizers, catalyst residues from their manufacture, organic and inorganic fillers such as calcium carbonates, clays, barium sulfate used as the radiopaque filler for medical devices, carbon blacks and other pigments, and the like, are also suitable as substrates for plasma treatment in accordance with the methods of the present invention.

The plasma treatment procedures of the present invention have been found to fade very slowly over a period of months. It is not certain whether this is associated with oxidative degradation of the functional groups attached to the substrate surfaces, or some other gradual decay processes. A preferred practice consists of coating the medical device within two months, or less, after the plasma treatment of the substrate material from which the device is fabricated has taken place. The highly preferred method consists of coating the plasma treated medical devices within two weeks, or less, after plasma treatment of the substrate material with the ammonia or organic amine plasma gases, or mixtures thereof. Like conditions apply for the twofold plasma treatments comprising oxygen-containing and nitrogen-containing plasma gases.

For the purpose of affixing rapidly reacting primary and secondary amino groups onto the surfaces of metal substrates or metal components, such as braided guidewires, metal tubing, and other metal components utilized in the medical devices of the present invention, it is feasible to treat such substrates with organosilane compounds having reactive aminoalkyl moieties that are attached to the silicone molecule. Such aminosilanes hydrolyze rapidly in water and the resulting silanols can react and condense with reactive species of the metal surfaces to form quite stable cohesive anchor bonds therewith. The amino ends of the hydrolyzed and condensed aminosilane are now available for reaction with functional groups such as for example isocyanate groups of the prepolymer coating intermediate of the present invention. Hence, the aminosilane primer treatment on the metal surface exerts a similar effect as, for example, the ammonia or organic amine plasma treatments of plastic substrates.

Typical aminosilanes which are suitable for priming the metal surfaces of the devices contemplated by the present invention include, by way of example, γ-aminopropyltriethoxysilane (A-1100; UNION CARBIDE), an aqueous prehydrolyzed aminoalkyl silanol solution (A-1106, prehydrolyzed A-1100), γ-aminopropyltrimethoxysilane (A-1110), N-beta-(aminoethyl)-γ-aminopropyltrimethoxysilane (A-1120), and the like. Typical aqueous aminosilane priming compositions contain from about 0.5%, by weight, to about 3% by weight, of the aminosilane compound in water. After applying the hydrolyzed aminosilanes to the metal device by dip-coating or other means, moisture and alcohols from hydrolysis are removed by evaporation, and the primed surface is coated with the hydrophilic PU urethane (PU/UR) adduct intermediate of the present invention in the usual manner to form the resulting hydrophilic PU/UR intermediate layer on the metal substrate. After evaporation of the coating solvent, the device is then subjected to the aqueous solution of the dissimilar hydrogel polymer to form the "commingled" slippery surface coating according to the standard method employed in the present invention.

According to the present invention isocyanate prepolymers which may be used for the preparation of the hydrophilic polyurethane coating intermediates include prepolymer reaction products of water-soluble mono- or polyfunctional polyethers, copolyethers, and block copolyethers from 1,2-alkylene oxide and alternatively copolyethers from 1,2-alkylene oxides and tetrahydrofurane or tetrahydropyrane and organic polyisocyanates selected from the group consisting of aliphatic, cycloaliphatic, araliphatic, aromatic and heterocyclic polyisocyanates, and derivatives thereof. Preferred polyethers employed as starting materials for such isocyanate prepolymer intermediates include water-soluble homopolyethers of ethylene oxide, copolyethers of ethylene and propylene oxides, copolyethers of ethylene and 1,2-butylene oxides, copolyethers from mixtures of all the above 1,2-alkylene oxides, and copolyethers of ethylene oxide and tetrahydrofuran. Highly preferred copolyethers are di- and trifunctional copolyethers from about 70% to about 85%, by weight, of ethylene oxide and from about 15% to about 30%, by weight, of propylene oxide. The copolyethers containing as much as from about 17.5% to about 25%, by weight, of propylene oxide are particularly preferred because they are liquid at room temperature, which greatly facilitates the handling of the resulting prepolymer adducts, because they also remain liquid at temperatures appreciably below room temperature. The moderate levels of propylene oxide do not detract from the solubility of the resulting copolyethers in water, and the hydrophilicity of the final hydrogels from said copolyether/polyisocyanate adducts are eminently suitable for the manufacture of lubricious wear-resistant hydrogel coatings. Such properties are further advanced by "commingling" the PU/PUR hydrogel with at least one or more dissimilar hydrogel polymer(s) belonging to the group of readily water-swellable hydrogels form polysaccharides, various salts thereof, especially alkali salts, high molecular weight poly(ethylene oxides), and PVP polymers, having MW's of from about 10,000 to about 340,000.

Methods for the manufacture of such water-soluble polyfunctional homopolyethers and copolyether polyols as well as monofunctional homopolyether and copolyether alcohols are well known in the art. Typically, monofunctional polyether alcohols and polyfunctional polyether polyols are derived by the addition of 1,2-alkylene oxides to monohydric alcohols or phenols, or polyhydric alcohols or phenols in the presence of alkaline catalysts. Copolyether diols from ethylene oxide and tetrahydrofurance, or larger ring cyclic oxides, are generally made in the presence of Lewis acids as the catalysts, as is well known in the art. Representative monofunctional and polyfunctional starters for the 1,2-alkoxylation reactions are, by way of example, methanol, ethanol, isopropanol, butanol, amyl alcohols, hexanol, 2-ethylhexanol, lauryl alcohols and other fatty alcohols, phenol, cresols, higher alkyl phenols, naphthols, and the like; water, ethylene glycol, diethylene glycol, propylene glycol, dipropylene glycol, 1,4-butanediol, 1,6-hexanediol, neophentylene glycol, resorcinol, hydroquinone, bisphenol A, xylenols, glycerol, trimethylolpropane, pentaerythritol, α-methyl glucoside, sorbitol, and the like. Water and lower carbon glycols are generally preferred starters for difunctional polyethers and copolyethers, whereas lower carbon trifunctional hydroxyl compounds are usually preferred starters for the manufacture of trifunctional polyether and copolyether intermediates. Although higher functional compounds, e.g., tetrafunctional and hexafunctional hydroxyl compounds can be used, they are generally not available as higher MW versions of commercial products. Ethylene and diethylene glycols or propylene and dipropylene glycols are highly preferred starting materials for the manufacture of difunctional copolyetherdiols, and glycerol and trimethylolpropane are highly preferred starters for the manufacture of trifunctional copolyethertriols from ethylene and propylene oxides.

The di- and higher-functional hydroxyl-terminated polyether and copolyether alcohols and polyols used as starting materials for the manufacture of hydrophilic isocyanate prepolymers of the present invention have equivalent weights (EW) per hydroxyl in the range of from less than about 500, to greater than about 20,000. Within this general range, preferred EQ's for difunctional polyetherdiols and copolyetherdiols are from about 1,000 to about 10,000, and highly preferred values range from about 1,500 to about 5,000. Further within the above broad ranges, preferred EQ ranges for the glycerol and trimethylolpropane copolyethertriol adducts from 1,2-ethylene oxide and 1,2-propylene oxide are from about 1,500, and lower, to about 7,500, or higher, while the most preferred EW ranges for these trifunctional products is from about 1,750 to about 2,750. The EW values of these polyetherdiols and higher-functional polyetherpolyols can be determined by phthalation or acetylation of the hydroxyl group by well known analytical techniques, such as, for example, ASTM Method D-4274-88.

As is well known, the above-described polyether adducts from 1,2-alkylene oxides are normally prepared by means of base catalyzed oxide addition to mono- and polyhydric alcohols or phenols. Typical oxyalkylation catalysts are hydroxides and alkoxides of alkaline earth metals such as sodium and particularly potassium. Representative of such catalysts are potassium and sodium hydroxide for the manufacture of polyfunctional polyethers, and sodium and potassium alkoxides of lower monohydric alcohols and phenols such as the methoxides, ethoxides, phenoxides, and the like, when the desired polyesters are intended to be monofunctional. Such catalysts are generally used at levels of from about 0.05% to greater than about 0.3%, by weight, based upon the oxide adducts being made. However, catalyst residues must be removed prior to the reactions with polyisocyanates, because they will catalyze unattractive side reactions of isocyanates, such as trimerization and dimerization of isocyanates, or formation of allophantes from urethanes formed during the prepolymer step, formation of urea and biuret derivatives, or additional undesirable by-products. Consequently, they must be removed by way of ion exchange reactions or other means after the oxyalkylation step. Similarly, if the polymerization is performed with acidic catalysts such as Lewis acids, they must also be removed by known methods, because they will slow down the reaction of the isocyanate group with hydroxyl-terminated polyethers. The presence of undesired alkali metals can also be examined by well established analytical procedures (ASTM D-4668-87). In this regard, the total presence of sodium and potassium metals in the polyethers should be within the range of from 0 to 10 ppm, preferably less than about 5 ppm, to avoid complications during the prepolymer reaction step.

Furthermore, it is important that the hydroxyl-containing strongly water-absorbing polyethers contain very low levels of water prior to their reaction with polyisocyanates to form the corresponding prepolymers. Moisture can lead to urea group formation and subsequent gelation of such prepolymers by means of biuret crosslinking reactions which interferes with the subsequent coatings steps. Consequently, it is advisable to dry such polyethers by means of azeotropic distillation with aromatic hydrocarbons such as toluene or xylenes, by careful drying under vacuum at 100° to 120° C. at pressures of from less than about 5 Torr to about 10 Torr, or by combinations of azeotropic distillation and vacuum drying. These procedures are well known in the art.

After removal of catalysts, the resulting polyetherdiols and higher functional polyether polyols must be protected from oxidation in the presence of air by means of antioxidants. Most of the antioxidants used in commercial practice are not biocompatile and are not useful for applications involving medical devices of the type employed for clinical uses in body fluids. However, on account of the relatively short insertion times of the medical devices of the present invention, antioxidants such as IRGANOX 1010, IRGANOX 1076 (CIBA-GEIGY), SANTONOX R (MONSANTO), and similar compounds can be considered to be acceptable for relatively short use in the bloodstream, since they have exhibited a low order of toxicity in other applications. The antioxidant level is generally at from about 0.01% to about 0.05%, by weight, based on the hydroxy-terminated polyether intermediate.

Suitable polyisocyanates for the manufacture of the hydrophilic polyether and copolymer prepolymer intermediates of the present invention include aliphatic, cycloaliphatic, araliphatic and heterocyclic polyisocyanates of the type described by W. Siefken in Annalen der Chemie, Volume 362, pages 75–136, and in many other publications well known in the art. Particularly preferred polyisocyanates include the commercially available diisocyanates such as 1,4-tetramethylene diisocyanate (DUTCH STATE MINES), 1,6-hexamethylene diisocyanate (HDI), trifunctional biuret and isocyanate derivatives of HDI (MILES CORPORATION, Polymers Division; OLIN CORPORATION, Olin Chemicals), isophorone diisocyanate (IPDI), the isomer mixtures of methylene bis(4-cyclohexylene diisocyanates) known as DESMODUR W® (MILES CORPORATION, Polymer Division), m-xylylene diisocyanates, m-tetramethylxylylene diisocyanate known as TMXDI-meta® (CYTEC INDUSTRIES, Inc., Stamford, Conn.), p-tetramethylxylylene diisocyanate, the isomer mixture of bis(isocyanataomethyl)1,3-cyclohexylene (MITSUBISHI GAS CHEMICAL CO., Inc., Toyko, Japan), and trans 1,4-cyclohexylene diisocyanate. A number of the above-described di- and poly-isocyanates are commercially available. Most of them are known to yield biocompatible polyurethane polymers, since they are known to yield amine hydrolysis products which are known to exhibit very low toxicity. This has been demonstrated in the case of HDI, IPDI, DESMODUR W®, and is expected to be valid for TMXDI and other commercially available diisocyanates listed herein above. Highly preferred polyisocyanates for the purpose of the present invention include aliphatic, cycloaliphatic, and araliphatic isocyanates. On account of commercial availability, particularly preferred polyisocyanates include 1,6-hexamethylene diisocyanate, and especially its trifunctional isocyanate and biuret derivatives, all of which exhibit low toxicity, isophorone diisocyanate and its trifunctional isocyanate derivatives, DESMODUR W®, AND TMXDI-meta®.

For the purpose of the present invention, the hydrophilic polyether and copolyether prepolymers adducts prepared from the above described polyethers are preferably reacted with about two equivalents of the isocyanate component per equivalent of the polyether hydroxyl compound to react most, if not all, of the hydroxyl groups which are available for conversion to the corresponding urethane polymer. In addition, it is also feasible to utilize the above diisocyanates as chain-extension agents to increase the chain length of difunctional prepolymers derived from polyether diols or copolyether diols. In this case, the relative ration of the reactants is adjusted accordingly to compensate for the chain lengthening action. In most cases the aliphatically attached isocyanate groups are either sterically hindered, attached to secondary carbon atoms (=CH—NCO) or tertiary carbon atoms [—C(CH$_3$)$_2$—NCO], for example, such as in TMXDI, all of them contributing sufficiently to slow down of prepolymer formation as to necessitate the use of isocyanate catalysts for the formation of the prepolymers. With a few somewhat faster reacting polyisocyanates, such as for example, HDI and its derivatives, other straight-chain non-hindered alkylene diisocyanates, or m- and p-xylylene diisocyanates the prepolymer adduct reaction can be conducted without a catalyst, if desired. However, even with these materials the catalytic prepolymer process is usually more cost-effective.

With the possible exception of TMXDI which is only moderately toxic as the free diisocyanate, in all other cases it is prudent to conduct the prepolymer formation is such manner as to minimize the presence of unreacted free diisocyanate. This is feasible by judicious selection of the NCO/OH reactant ratios and/or selection of the appropriate catalysts and catalyst levels during the formation of the prepolymers. Furthermore, it is also feasible to remove unreacted free diisocyanates by means of thin-film evaporators, a procedure well known in this art. In the case of the highly hindered and slow reacting diisocyanates the use of the catalysts is definitely recommended and is, in fact, essential to react substantially all the hydroxyl groups of the starting polyether polyol intermediates.

The reaction for the prepolymer adduct formation comprising the manufacture of polyurethane prepolymers from the polyether polyols of the present invention and the slow reacting cycloaliphatic isocyanates DESMODUR W® and IPDI as well as all other slow reacting polyisocyanates, is preferably conducted in the presence of tin catalysts to achieve acceptable conditions of manufacture. Typical tin catalysts which are useful for this purpose include dialkyltin diacylates, dialkyltin oxides, and stannous acylates, because they are not known to catalyze trimerization reactions of such isocyanates and they are powerful catalysts for the hydroxyl-isocyanate reaction. Preferred tin catalysts are the commercially available tin compounds, for example dibutylin dilaurate and stannous octoate, which have been found to give excellent results at concentrations of from 10 to 20 ppm at reaction temperatures of from about 50° C. to about 75° C. and reaction times of from about 2 hours to not more than about 6 hours. The moderate catalyst levels also make these materials suitable for biomedical uses, which is an important aspect of the present invention. In contrast thereto uncatalyzed reactions with the above isocyanates and poly-ether polyols were incomplete after even 12 to 24 hours. Although it is also feasible to catalyze the isocyanate prepolymer reactions with tertiary amines, and many other transition metal catalysts other than tin compounds, their use is not very desirable for the purpose of the present invention because most of them are toxic and not biocompatible, and also because most of them also catalyze the isocyanate trimerization reaction which often leads to premature gelation of the isocyanate prepolymers.

In the case of the faster reacting straight-chain alkylene diisocyanates and unhindered araliphatic diisocyanates the prepolymer adduct formation can be carried out without tin catalysts, if desired. Typical reaction conditions involve reacting such faster reacting polyisocyanates with the poly-etherdiols and polyols of the present invention at temperatures from about 70° C. to about 90° C., for a period of from about 4 hours to about 12 hours, or longer. The final NCO content of the finished prepolymer adduct can be determined by the wet chemical dibutylamine analysis method or similar analytical procedures (ASTM D-4666-87).

It is within the scope of the present invention to conduct the prepolymer formation in the presence of suitable solvents to facilitate handling of process ingredients, moderate the exothermic reaction processes, as well as to obtain solutions of the prepolymers before making up the final coating compositions that involve the same or other solvents than the ones utilized in the reaction step. The use of moderate amounts of solvents during prepolymer formation is a preferred operating procedure because the resulting intermediates exhibit lower viscosities and better handling and storage characteristics. For the purpose of achieving suitable reaction conditions during the prepolymer formation step, the total solids content of the reactants utilized in the prepolymer synthesis can vary over a wide range, for example from about 20%, by weight, to as high as about 80%, by weight. A preferred range is from about 30%, by weight, to about 70%, by weight, and a most preferred range is from about 40%, by weight, to about 60%, by weight. The solvents which are utilized in the prepolymer process should be free of water ("urethane-grade" solvents), and non-reactive with the isocyanates used in the process. Such solvents or often commercially available or can be dried suitably by means of molecular sieves, a procedure well known in the polyurethane art. Solvents which are particularly useful for the prepolymer formation are aromatic hydrocarbons such as, for example, benzene, toluene, xylenes, and the like. A highly preferred solvent concentration for the reaction is from about 40% to about 60%, by weight, of solvent, and after completion of the reaction, the same solvent is preferably utilized for dilution to about 25%, by weight, solids content for convenient storage of the intermediate. Such solvents are also useful for non-catalyzed prepolymer adduct formation, because the procedure facilitates handling of the often highly viscous prepolymer materials prior to subsequent dilution with other solvents to the desired coating compositions and dilutions. The solvents which are utilized in the prepolymer process should preferably have a boiling point above the reaction temperature employed for the prepolymer formation, but should boil low enough to allow convenient evaporation of the diluents after the subsequent coating operation of the plasma-treated material of the medical device or other object. Furthermore, the solvents should not be detrimental to the materials of construction used as the substrate material of the medical device during the subsequent coating operation. Aromatic hydrocarbons are generally highly preferred for this purpose, because they are nonaggressive in this respect, but they are also excellent solvents for the achievement of homogeneous reaction conditions because the polyether polyols and the isocyanate reactants of the present invention are mutually soluble.

The final coating solution containing the hydrophilic PU prepolymer adduct intermediates is diluted to the desired concentration by means of relatively low boiling solvents such as, for example, pentanes, hexanes, methylene chloride, acetone, methylethyl ketone, methyl tert. butyl ether, or other solvents which can speed up the evaporation after coating of the plasma- or aminosilane-treated substrates. Typical solids contents of the coating solutions can vary from about 1% polymer solids, by weight, to about 20%, or higher. Preferred solids contents can vary from about 1.5%, by weight, to about 8%, by weight, and highly preferred coating solutions are those having polymer solids contents of from about 2%, by weight, to about 4%, by weight. Such coatings are applied by means of dip-coating, spraying or other means. After deposition of the coating it is allowed to dry at temperatures varying from about room temperature to around 60° C. During the coatings deposition, a portion of the NCO groups of the PU prepolymer adduct intermediate react with the amino groups that are deposited on the treated polymer or metal surfaces and form the hydrophilic PU/UR prepolymer adduct which is now covalently attached to the substrate surfaces. After evaporation of the solvent, the device is immersed into an aqueous solution or dispersion of the dissimilar hydrogel polymer and forms the final "commingled" hydrogel of the different hydrophilic polymers.

Finally, the water-soluble dissimilar hydrogels of the present invention can also include low, medium, and high molecular weight versions of poly(n-vinylpyrrolidone) having MW's of from about 10,000 to about 340,000. They can be used as dilute aqueous solution during the preparation of the "commingled" hydrogel polymers with the hydrophilic PU/UR prepolymer adduct of the present invention. It is unlikely that the POLYOX® polymers can partake in grafting reactions, because they normally do not contain NCO-reactive groups, but it is believed that they form complex polymer networks with the PU/PUR hydrogel polymers, or they form association polymers during the formation of the hydrogel polymers from the PU/UR prepolymers of the present invention. In any case, the aqueous hydrogel formation with the water-soluble hydrogel of the dissimilar polymer yields lubricious, wear resistant and unexpectedly permanent commingled barrier coatings that perform very well when tested in blood. The present process is more cost-effective than previous procedures suggested for "slippery" coatings from POLYOX® polymers.

The formation of the "commingled" hydrogel polymers involves reacting the hydrophilic PU/UR polymer adducts of the present invention with water and, optionally, with reactive polyamine chain extenders, which are dissolved in the dissimilar aqueous polysaccharide polymers, their metal salts, the poly(ethylene oxide) homopolymers, or the PVP hydrogels, and can be performed as a catalyzed or non-catalyzed reaction. Typical catalysts which can be utilized to accelerate the hydrogel formation are various tertiary amine catalysts, well known in the polyurethane art. They can include relatively high boiling water-soluble tertiary amines, but the use of low boiling water-soluble tertiary amine catalysts is highly preferred because they can be removed readily from the coating by the application of moderate heat and vacuum. Typical water-soluble low boiling amine catalyst that are suitable for this purpose include N-trimethylamine, N-dimethylethylamine, N-methyldiethylamine, N-triethylamine, N-tripropylamine, N-dimethylpropylamine, N,N'-tetramethyl ethylenediamine, and the like. However, it is important that they be removed from the hydrogel coating by means of washing with water, or preferably by distillation techniques to avoid their contact with human tissue, or cellular fluids to avoid irritation or biocompatibility problems. Typical catalyst levels for the above tertiary amines in the aqueous hydrogel polymer should be in the range of from about 0.01%, by weight, to about 0.2%, by weight, or higher, to reduce the formation time of the "commingled" hydrogel polymers at room temperature from around 6 to 8 hours, or less, to about 30 minutes, or less. However, although the use of such catalysts is highly recommended, care must be taken to make sure they are removed before use of the clinical device. The concentration of the dissimilar hydrogel polymers in water varies from about 0.25%, or less, by weight, to 2.5%, or more, by weight, depending upon the molecular weight of the polymer and the viscosity inherently associated with such solutions.

A more preferred catalytic method for the formation of the "commingled" hydrogel polymers of the present invention involves the use of water-soluble reactive di- or higher functional amines in the aqueous dissimilar hydrogel polymer to effect a rapid formation of the "commingled" PU/UR hydrogel polymer. This technique has the inherent advantage that the reactive polyamine is consumed during the hydrogel formation making the removal of the catalyst only a minor problem, if any. The polyamines are incorporated into the hydrogel polymer as urea groups which are formed instantaneously upon contact with the free isocyanate groups of the PU/UR hydrogel intermediate which is attached to the polymeric or metal substrate. Typical water-soluble reactive polyamines of this type include, by way of example, ethylenediamine, 1,2-propylenediamine, 1,3-propylenediamine, 1,4-butanediamine, 1,6-hexanediamine, diethylenetriamine, piperazine, and the like, or mixtures thereof. Ethylenediamine is a highly preferred reactive water-soluble reactant. The catalyst concentration of the reactive diamines is held within the range of from about 0.01%, or less, by weight, to about 0.25%, or higher, by weight, to effect rapid cure of the "commingled" hydrogel polymers at a temperature of from room temperature to slightly higher. With this technique, the hydrogel formation occurs within a period of time of from about 30 minutes, or less to about 4 hours, or less, depending upon the reactive catalyst concentration and dip-time during the immersion procedure, which varies from 30 seconds, or less, to as much as 10 minutes, or longer, if desired. Optimized conditions are best determined by experimental coating procedures followed by measuring the physical characteristics of a coated specimen in bovine blood according to the conditions described hereafter.

Although the hydrogel coatings of the present invention can be stored in the wet state, it is preferable to transform them to the dry state by means of evaporation of the large amount of moisture which is present in the hydrogels. The device can be sterilized before or after drying by conventional methods used in the art. The removal of the moisture from the hydrogel can be conducted at slightly elevated temperatures, for example, at from room temperature to about 50° C., or higher, while the device is exposed to a vacuum of from about 5 Torr, or less, to around 20 Torr, or higher, for a sufficient time period to remove substantially all moisture. Upon exposure to saline solution or other aqueous media before clinical use, the hydrophilic surface coating is fully regenerated to its previous characteristics within a short time period, for example from 1 to 2 minutes, or less.

The following examples are further illustrative of various aspects of the present invention. They are not deemed to be limiting in any way. The scope of the present invention is set forth by the set of claims appended hereto. Other embodiments of the various aspects of the invention within the scope of the claims will be evident to those skilled in the art. The examples describe all of the several parameters involved in plasma-treating the substrate polymers, preparing the hydrophilic isocyanate prepolymers of the present invention, affixing them covalently to the treated substrates, and then converting the attached hydrophilic topcoats to the lubricious hydrogels by simultaneously commingling them with at least one other dissimilar aqueous hydrogel polymer in one step to form the final lubricious hydrogel of the present invention. They also demonstrate the mechanical performance of coated devices, their wear resistance, and their resistance to the exertion of mechanical drag forces in blood. The examples also outline a suitable procedure for the measurement of both the dynamic behavior and permanence of the lubricious coatings of the present invention in blood.

DEFINITIONS

As used in the Examples appearing below and in the specifications, the following designations, symbols, terms, and abbreviations have the indicated meanings:

1. Molecular weights (MW) of polyols are number average molecular weights using the experimentally determined hydroxyl numbers of the polyols in accordance with ASTM D-4274-88, assuming that the functionally is known.
2. Equivalent Weights (EW) of polyols are number average equivalent weights of polyols as calculated on the basis of analytically determined hydroxyl numbers.
3. Isocyanate Equivalent Weights (EW/NCO) are number average equivalent weights of isocyanate prepolymers calculated on the basis of determination of % NCO of said prepolymers in accordance with ASTM D-4666-87 and/or equivalent test methods known in the art. For commercial monomeric diisocyanates, their derivatives, and HYPOL PreMA-G-50 prepolymer, published data exist.
4. "ml" denotes milliliters.
5. "Torr" denotes millimeters (mm) of mercury pressure [1 atmosphere=760 Torr (mm Hg)].
6. "ppm" denotes parts per million (catalyst concentrations, metals contents).
7. AMBERLYST 15 (ROHM & HAAS) denotes a strongly acidic macroreticular ion exchange resin, generally used for non-aqueous reactions.
8. AMBERLYST A-21 (ROHM & HAAS) denotes a weakly basic macroreticular ion exchange resin for removal of acidic anions from non-aqueous systems.
9. "Urethane-grade" denotes specially dried and/or distilled solvents used as diluents for the isocyanate prepolymer reactions and prepolymer coatings solutions of the present invention (driers normally comprise UOP molecular sieves, type 4A, or equivalent materials).
10. "Silicone" Coating comprises a 2% solution of DOW CORNING MDX4-4159 Fluid in n-heptane applied to the device. According to the DOW CORNING MSDS Data Sheet, MDX4-4159 is a solution containing 34% Stoddard Solvent, 15% isopropyl alcohol, 1% dimethyl cyclosiloxanes, and 50% of dimethoxy silyl dimethyl aminoethyl amino propyl silicone polymer (all constituents are expressed in %, by weight).
11. "Ringer's Solution" is an isotonic saline solution comprising 0.86 gm of NaCl, 0.03 gm of KCl, and 0.033 gm of $CaCl_2$ in 100 ml of purified water.
12. "Footnotes 1 to 17" in Example 1, Table 1 describe the chemical nature of water-soluble polyether reactants and the polyisocyanates used for the preparation of the hydrophilic polyether prepolymers of the present invention.
13. HYPOL PreMa® G-50 comprises a hydrophilic polyether prepolymer based on IPDI (isophorone diisocyanate) available from HAMPSHIRE CHEMICAL CORP., Lexington, Mass., containing approximately 0.4 milliequivalent of NCO/gm.
14. A parison is a rod-like or tubular blank from which a balloon for a medical device is subsequently formed by blow-molding. Parisons are formed by direct extrusion of the plastic substrate material. Plastic parisons are useful as test substrates, and were used in the examples herein, because their geometric uniformity makes them easy to plasma-treat, and because they are readily adapted to drag force measurements.
15. The term hydrophilic refers to substances on which water droplets do not readily form beads on the surface of such substances, but, instead, the water droplets tend to assume a contact angle of less than 90° with the substance, and readily form a film on the surface of the substance. Hydrophilic substances may also tend to absorb water and swell to weights much greater than their dry weights.

EXAMPLES

Dynamic Drag Force Test Method

For the purpose of measuring drag forces on coated catheter tubes or balloon devices used in coronary angioplasty, it was necessary to develop an applicable test method which gave reliable comparisons with the prior art and between the different polymer compositions of the hydrophilic coatings of the present invention. Moreover, it was also decided to conduct the tests in different aqueous media, for example distilled water, saline solution (Ringer's Solution), blood plasma and in blood to investigate the influence of the most critical use environment the clinical devices can experience.

The test method for the measurement of friction and permanence for the antifriction coatings on plastic tubes of the present invention consisted of the following procedure:

Apparatus: INSTRON Tensile Tester, 20 lb load cell; test range 0–500 gm; cross head speed 20 inches/min up and down; 4 inch stroke, automatic cycle.

Test Fixture: Clamshell assembly with friction surface for holding coated plastic tube specimens. The friction surface was a commercial cleaning product SCRUNGE® available from Guardsman Products, Inc., Consumer Products Division, Grand Rapids, Mich. and sold in major food markets. The SCRUNGE® pad, consisting of ground rigid abrasive PU plastic particles surface-coated onto a flexible polyurethane foam matrix, was cut into 1×1.75 inch rectangles. The friction surfaces were moistened with the wetting fluid and folded in half with the abrasive surface inside. The tubular test specimen was enclosed in the folded friction surface and placed in the test fixture.

Test Parisons: The test parisons were thin well plastic tubes, having a length of from about 6 to about 8 inches, and an outside diameter (OD) of from 0.07 to 0.095 inch, and an inside diameter (ID) of from 0.04 to 0.07 inch. In the event the test sample was too flexible and buckled during the return cycle, a 0.066 inch OD braided wire rod was inserted into the test specimen (HYTREL and other relatively flexible tubing).

Wetting Medium: The wetting media tested were distilled water, Ringer's Solution, blood plasma, and defibrinated beef blood. The medium was delivered continuously to the tube at the top of the test fixture at the rate of 10 to 20 drops per minute, by means of capillary tubing using a syringe pump.

Test Procedure: A braided wire shaft was placed in a test sample, as necessary. The friction surface was wetted with appropriate test fluid. The friction surface was folded over the test sample, and the combination of the two was placed into the test fixture and the fixture was closed. The top end of the test sample was clamped into a clamp on the load cell. The INSTRON test machine was started, and drag force measurements were recorded at 1, 5, 10, 20, and 40 strokes.

Example 1

Rectification of Hydrophilic Polyether Precursors Based on Commercially Available Compounds for Use in Prepolymer Syntheses Initially the starting material selected for the evaluation of PU hydrogel materials to be affixed to ammonia plasma-treated surfaces consisted on HYPOL PreMa® G-50, a commercially available PU hydrogel intermediate based on isophorone diisocyanate (IPDI) and a water-soluble copolyether polyol. This prepolymer has a structure that appeared suitable for the preparation of the PU hydrogels of the present invention. Furthermore, it was represented to yield biocompatible polyurea polymers that appeared quite slippery. Consequently, this product was examined first in the attempt to perfect covalently-bonded hydrogels to ammonia plasma-treated substrates of interest for medical devices. However, it became soon apparent that this product contained very appreciated quantities of unreacted copolyether hydroxyls.

Commercially water-soluble homopolyethers and copolyethers containing from one to about three hydroxyl groups per macromolecule were selected as the first choice for starting materials for the synthesis of the prepolymers of the present invention. Most of these materials soon proved unsuitable because they contained sufficient quantities of alkali metals or alkali metal salts to interfere with the prepolymer reactions. Consequently, the products were ion-exchange treated by dissolving them at concentrations of about 50%, by weight, in solutions of isopropyl alcohol and stirring with excess quantities, in relation to estimated levels of metal catalyst impurities present, of about equal quantities of AMBERLYST 15 and AMBERLYST A-21 which had been preconditioned by immersion in isopropyl alcohol in order to remove the alkali metals and their salts. Some of the homopolyethers of ethylene oxide were solids at temperatures as high as 50° to 55° C. and in those cases, the isopropanol/polyether mixture was heated to about 60° C. and maintained there during the ion exchange reaction. In all other cases the ion exchange treatment was conducted at from room temperature to about 40° C. Alternatively, the ion exchange refining is conducted in a continuous manner by means of mixed bed heated columns or separate columns using the cationic and anionic resins separately, as is well known in the art.

A slurry of the mixed ion exchange resins in the polyether/isopropanol dilution was agitated for a period of at least 6 hours. After that time, the resins were removed by filtration, and the ion exchange resins were washed with a portion of isopropyl alcohol to remove entrained polyether therefrom. For the homopolyethers from ethylene oxide, the rinse was conducted with preheated isopropanol (~60° C.). The rinse solutions were combined with the original filtrate for subsequent evaporation of the diluent and water present in the polyethers. Before handling the polyether materials at elevated temperatures in the presence of any air, they were protected by means of suitable antioxidants. For this purpose, a quantity of about 0.05%, by weight, based upon the original weight of polyether used for refining, of SANTONOX R (see also U.S. Pat. No. 4,886,866), was added and dissolved before subsequent solvent stripping operations.

The isopropyl alcohol was removed by distillation while blanketing the vessel with a slow stream of dry nitrogen to avoid contact with air. After distillation of the alcohol ceased, a small quantity of toluene or xylenes were added to the polyether residue and the materials were subjected to a gradually increasing vacuum. During this procedure, water and remaining traces of isopropanol were removed by means of azeotropic distillation. Finally, the polyether residue was subjected to a vacuum of from 5 to 1 torr at 100 to 120° C. for a period of 2 to 3 hours under a blanket of dry nitrogen. After this time, the polyether residue was allowed to cool to about 70° C., the vacuum was then discontinued while the vessel was brought to atmospheric pressure by means of blanketing with dry nitrogen. The polyether product was alternatively removed while still warm or was utilized directly for the prepolymer formation step. The polyether precursor was analyzed for hydroxyl number, % $H_2O$, (ASTM D4672-87), and ppm alkali metals, as necessary. To avoid complications due to side reactions from moisture, rehydration of the polyols was prevented by storing them under carefully monitored anhydrous conditions.

Example 2

Preparation of Hydrophilic Cycloaliphatic Isocyanate Prepolymers from Commercially Available Ion-Exchanged Polyether Precursors Because of the unsuitability of prepolymers prepared using the commercially available water-soluble homopolyethers and copolyethers of Example 1, it became necessary to explore the preparation and composition of a number of cycloaliphatic isocyanate prepolymers that appeared useful as starting materials for the PU hydrogels of the invention.

For the purpose of preparing the prepolymers designated A through E, H through M, and O and P, presented in Table 1, the polyether starting materials were heated to about 30° C. for materials which were liquid at room temperature, and to about 55° C. in the case of the solid homopolyethers, and the reactants were maintained throughout the procedure under a blanket of dry nitrogen. At this point the appropriate amount of catalyst, if any, was added to the reaction vessel. The calculated amount of diisocyanate was then added all at once, while the reactants were mixed thoroughly to effect immediate homogenous reaction conditions. The ensuing exotherm was moderated if necessary to attain a reaction temperature of 70° to 75° C., and the reactants were held at this temperature for a total of about 4 hours for the catalyzed reactions, and up to 24 hours for the non-catalyzed systems.

It was found that the reaction between the polyethers and the cycloaliphatic isocyanates DESMODUR W and IPDI were incomplete even after even 24 hours at the above reaction temperatures in the absence of catalyst. Consequently, the prepolymer synthesis procedure was eventually amended to use tin catalysts (dibutyltin dilaurate or stannous octoate) for all prepolymer syntheses with these relatively slow reacting diisocyanates. It was also discovered that it was easier to moderate the isocyanate reaction in the presence of aromatic hydrocarbons which were co-solvents for the polyethers and the cycloalophatic isocyanates. The solvent which proved to be most useful was toluene, and the reactions were generally conducted as 50% dilutions between reactants and solvent, but it was also feasible to use 75% toluene and 25% reactants, if warranted. The solvent procedure also facilitated handling of the prepolymer materials for subsequent dilution with other solvents to the desired coatings compositions.

At the end of the prepolymer synthesis, the resulting products were analyzed for % NCO by the wet method with dibutylamine, a procedure well known in the art. For catalyzed reactions, the desired EW/NCO agreed quite well with the calculated values. In the case of uncatalyzed reactions, only the somewhat faster reacting aliphatic diisocyanates (HDI) gave acceptable results. However, it was also established that in the case of IPDI, the NCO addition reaction to the polyether polyol could also be conducted at from 110° C. to 120° C. in a period of from about 12 hours to about 16 hours in the absence of catalyst without the formation of unsuitable trimer gels which occurs with normal aliphatic diisocyanates. Prepolymers containing polyethers having a propylene oxide content of at least about 15 to 20%, by weight, resulted in liquid polyether prepolymers that greatly facilitated handling of the coatings intermediates.

Table 1, entitled "Composition of Hydrophilic PU Prepolymer Intermediates", lists the compositions, characteristics and preparation conditions of the new intermediates:

TABLE 1

Composition of Hydrophilic PU Prepolymer Intermediates

| RUN # | POLYETHER | STRUCTURE OXIDE/FUNCT. | MOL. WT. | ISO TYPE | OH TO NCO EQ RATIO[1] | CATALYST | PE/gm | ISO/gm | CAT/gm | PHYSICAL STATE ROOM TEMP |
|---|---|---|---|---|---|---|---|---|---|---|
| A | PEG 2,000[2] | EO - DI | 2,000 | W[3] | 2:3 | T-9[4] | 125.2 | 24.66 | 0.044 | Solid |
| B | PEG 3,400[5] | EO - DI | 3,400 | W | 2:3 | T-9 | 134.4 | 15.55 | 0.046 | Solid |
| C | PEG 8,000[6] | EO - DI | 8,000 | W | 1:2 | T-9 | 131.7 | 6.98 | 0.049 | Solid |
| D | PLURACOL V-10[7] | EO/PO - TRI | 22,000 | I[8] | 1:2 | none | 64.8 | 1.82 | none | Liquid |
| E | PLURACOL V-10[9] | EO/PO - TRI | 22,000 | W | 1:2 | T-9 | 67.1 | 2.09 | 0.022 | Liquid |
| H | UCON 75-H 90,000[10] | EO/PO - DI | 15,000 | I | 1:2 | none | 65.0 | 1.93 | none | Liquid |
| I | UCON 75-H 90,000 | EO/PO - DI | 15,000 | W | 1:2 | T-9 | 62.5 | 2.19 | 0.022 | Liquid |
| J | PEG 14,000[11] | EO - DI | 14,000 | I | 1:2 | none | 70.0 | 2.22 | none | Solid |
| K | PEG 14,000 | EO - DI | 14,000 | W | 1:2 | T-9 | 70.7 | 2.65 | 0.022 | Solid |
| L | UCON 75-xH 9,500[12] | EO/PO - DI | 6,950 | I | 1:2 | none | 70.3 | 4.50 | 0.022 | Liquid |
| M | UCON 75-H-9,500 | EO/PO - DI | 6,950 | W | 1:2 | T-9 | 71.5 | 5.39 | none | Liquid |
| O | UCON 75-H-90,000 | EO/PO - DI | 15,000 | W | 1:2 | T-12 | 62.5 | 2.19 | 0.00129 | Liquid |
| P | HCC G-50 EOPO[13] | EO/PO - TRI | ~7,300 | I | 1:2 | T-12 | 73.17 | 6.67 | 0.0016[14] | Liquid |
| Q | PreMA G-50[15] | EO/PO -TRI | | I | 1:2.05 | none | — | — | none | Liquid |

[1]Reactant ratio - Equivalents of polyether hydroxyls to equivalents of NCO (ISO) compounds;
[2]Polyethylene glycol - MW ≅ 2,000;
[3]DESMODUR W, Cycloalipathic diisocyanate available from MILES CORP., Polymer Division; MW = 262.4, EW = 131.2;
[4]Stannous octoate; note: all uncatalyzed DESMODUR W systems tested contain free diisocyanate;
[5]Polyethylene glycol - MW ≅ 3,400;
[6]Polyethylene glycol - MW ≅ 8,000;
[7]Trifunctional copolyether polyol comprising trimethylolpropane adduct of 75/25 wt. % EO/PO - MW ≅ 7320, EW ≅ 2439;
[8]Isophorone diisocyanate, available from HUELS AMERICA, Inc.; MW ≅ 222.3, EW ≅ 111.15;
[9]Trifunctional copolyether polyol comprising trimethylolpropane adduct of 75/25 wt. % Eo/PO - MW ≅ 22,000, EW ≅ 7330;
[10]Difunctional copolyether diol comprising 75/25 wt. %, % EO/PO - MW ≅ 15,000;
[11]Difunctional polyethylene glycol - MW ≅ 14,000;
[12]Difunctional copolyetherdiol - MW ≅ 6,950;
[13]Precursor copolyether triol for HYPOL PreMA G-50 prepolymer (HAMPSHIRE CHEMICAL CORP.) believed to contain 75/25 wt. % of EO/PO; MW ≅ 7,300, OH No. ≅ 23.0;
[14]Systems O and P were also run as 50% solutions in toluene for ease of handling and subsequent dilution to desired coatings concentrations and compositions;
[15]HYPOL PreMA ® G-50; non-catalyzed isophorone diisocyanate (IPDI) prepolymer from copolyether (13) and IPDI - EQ ratio 1:2.05; contains free IPDI and free hydroxyls.

Example 3
Processes for Plasma Treatment, Intermediate Coating, and Formation of PU Hydrogels Plastic materials, having essentially no functional groups that were capable of reaction with the isocyanate group, were used to obtain covalent bonds with the hydrophilic hydrogel polymers of the present invention. Suitable such as PET, used in angioplasty balloons; HYTREL, used for catheter shafts; PE, used for various balloons; and hydrophobic nylon-11 and nylon-12 polymers, used in catheters and balloons, were considered as the most important thermoplastic polymer substrates for plasma treatment with nitrogen-containing gases to affix very reactive amino groups onto their surfaces. In the case of various types of very hydrophobic PE substrates, it was unexpectedly discovered that successive plasma treatments comprising a first treatment with oxygen-containing plasma gases, followed by a second plasma treatment with ammonia resulted in synergistic effects leading to considerably better bond formation than by plasma treatment with either of the two plasma gases alone. With the slow reactive isocyanate hydrogel intermediates of the present invention, the formation of cohesive bonds with substrates having no functional groups on their surfaces is virtually impossible to accomplish, and it is not always easy to obtain good permanence even with TPU and the hydrophobic nylon substrates which contain urethane and amide groups in their molecular structure. For the purpose of the plasma treatment studies, PET, HYTREL, and PE were utilized as the plastic substrates because they are typical surfaces that do not lend themselves to cohesive bonding unless the surfaces are either oxidized, treated with very aggressive solvents, or made reactive by other means. Plasma-treated test parisons of PET, PE, and HYTREL were therefore investigated very closely. It was the purpose of the experiment to prove that the affixation of amino groups upon the substrate surfaces would render them very reactive with the sluggish isocyanate groups of the hydrophilic prepolymers of the present invention. The resulting hydrogels are highly preferred because of their greater biocompatibility in comparison with polyurethane hydrogels derived from aromatic polyurethane hydrogel intermediates.

Ammonia ($NH_3$) was used as the plasma gas with the PLASMA SCIENCE PS 0350 Plasma Surface Treatment system, previously described in detail, and the experiment was conducted over a wide range of parameters. It was clearly established that for PET tubing (parisons having an OD of about 0.095 inches) use of $NH_3$ as the plasma gas resulted in improved adhesion of the PU hydrogel systems of the present invention, over an RF input range of from 20% power input (about 100 to 120 W) to 85% power input (about 400 to 450 W), at an ammonia gas flow rate of from about 50 std ml/min to about 730 std ml/min during exposure times of from about 30 seconds to about 3 minutes, and at a temperature in the range of from room temperature to about 40° C. Optimized results were observed and noted at from about 100 W to about 400 W power input, and ammonia flow rates of from about 200 std ml/min to about 650 std ml/min. ESCA surface analysis indicated that best permanence was achieved at intermediate surface concentrations of amino groups on the PET surfaces, although this method of surface analysis is not believed to be accurate enough to be absolutely reliable. Oxygen plasma was applied to various PE substrates under the above defined conditions, but adhesion results with the polyurethane intermediates of the present invention were at best marginal. When the oxygen plasma treatment was followed with a second treatment utilizing an ammonia plasma gas, bonding with the hydrophilic polyurethane intermediates of the present invention proved to be excellent. It was further observed that the combined plasma treatment with oxygen-containing plasma gases, followed by nitrogen-containing plasma gases, was better than when ammonia alone was used as the plasma gas. This unexpected observation indicates that a synergistic effect exists when utilizing treatment with both plasma types in succession.

The influence of the $NH_3$ plasma treatment was tested with commercially available "Silicone" coating on PET parisons in the presence of blood as the contact environment and compared with the PU hydrogel from HYPOL PreMA® G-50, catalyzed versions thereof, as well as combination systems comprising PreMA® G-50 and other PU hydrogel prepolymer coatings (see also Examples 1 and 2 for synthesis of hydrophilic PU intermediates). The "Silicone" coating was not helped by the $NH_3$ plasma treatment. Moreover, the "Silicone" coating did not show any kind of permanence in the presence of blood, the main body fluid tested. In contrast, the PU hydrogel coatings of the present invention, commingled with one or more dissimilar hydrogel polymers, exhibited remarkably improved permanence in blood after ammonia plasma treatment. Likewise, the double plasma treatment comprising oxygen and ammonia plasma for PE substrates exhibited very good permanence of the combination hydrogel polymers in blood as the test medium. Furthermore, it should be noted that even the PU hydrogels and combination hydrogels without plasma treatment of PET, for example, were found remarkably superior with respect to permanence in blood in comparison with the "Silicone" coating.

Range finding tests with respect to concentration effects of the PU hydrogel intermediates (Example 2 and others) showed that suitable hydrogel coatings on the substrate surface are possible when the solids content of the coatings solution is within the range of from about 1.5% to about 6%, and when the dip time is from about 10 seconds to about 30 seconds. However, it is within the realm and scope of the invention to stay at the lower concentration range or even below, if the dipping time is extended, or relatively more aggressive solvents are used during the initial dipping procedure. Various known contacting methods, including spray coating, are also feasible. The insertion time of the device into the coating solution has a pronounced effect upon the quality of the coating. Other measures which influenced the coatings thickness and quality were the use of somewhat higher boiling solvents such as cellosolve acetate (UCC) and other similar slower evaporating materials as co-solvents with the lower boiling products such as MEK, ethers, and the like. Other materials which proved useful for the achievement of uniform coatings included minute quantities of surface active agents, for example, TERGITOL® X-100 (UCC) and thixotropic agents, such as amorphous silicas and other materials which are known to influence the quality and application of coatings to various substrates.

A double coating procedure applying the hydrophilic polyurethane prepolymers of the present invention (for compositions, see Table 1 of Example 2, and Example 4) dissolved in appropriate relatively low boiling solvents, allowing the solvents to evaporate, followed by the application of at least one second dissimilar hydrogel polymer in dilute aqueous solution, gave the most promising results for the cost-effective formation of the commingled hydrogels of the present invention. The concentration of the dissimilar hydrogel polymer in water can be varied from about 0.25%, by weight, or lower, to around 2.5%, by weight, or higher, depending upon the viscosity of the resulting solution. The usefulness of such combinations was ascertained by testing various compositions in terms of the resulting drag force measurements and cycle testing for permanence of the coated parisons in blood after the completion of the hydrogel formation.

The formation of the commingled hydrogels was accomplished by means of coating the device, allowing the coating solvent to evaporate by various means, including the use of a forced air hood, and dip-coating the parison or device into aqueous solutions of varying compositions of one or more dissimilar hydrogel polymers. It was found useful to accelerate the hydrogel formation by means of tertiary amine catalysts, reactive amine derivatives, or in the presence of mildly basic salts, for example, the alkali metal salts of uronic acids in polysaccharides, to speed up the hydrogel formation. The influence of hydrogel-forming water in combination with dilute reactive amines dissolved in the aqueous solutions of the dissimilar hydrogel polymers, for example ethylenediamine and other polyamines, results in the formation of commingled PU/PUR hydrogel polymers with dissimilar hydrogel polymers which are the focal points of the combined lubricious hydrogels of the present invention. Although the hydrogel formation can be performed at relatively low temperatures, for example, at room temperature, alternatively, it can be conducted at higher temperatures, for example, at temperatures up to about 60° C., or higher, to speed up the cure times, and make the process less time-consuming and more cost-effective. Still other process variations of the present invention may readily be apparent to one skilled in the art.

Example 4
Catalytic Synthesis of Hydrophilic Prepolymers

This example demonstrates the preparation of hydrophilic prepolymers R and S, synthesized by the catalytic technique with 20 ppm of T-12 catalyst (dibutyltin dilaurate) as a 50% solution in toluene. In both cases the water-soluble polyether precursors were deionized by means of a slurry of AMBERLYST 15 and AMBERLYST A21 in isopropanol, and after filtration, the combined effluents were stabilized with 0.05%, by weight, of SANTONOX R. The isopropanol was then removed by distillation under atmospheric pressure until evolution ceased, and a small quantity of toluene was added and the distillation of toluene was continued to remove remaining isopropanol and moisture by azeotropic distillation while under a blanket of nitrogen throughout the refining cycle. The materials were then subjected to a vacuum of from about 5 Torr to about 10 Torr for a period of 3 hours at a temperature of from about 100° C. to about 120° C. The copolyether precursor was then charged to a prepolymer reaction flask, diluted with 50%, by weight, of toluene, and the required amount of T-12 catalyst, diluted in toluene, was added, while the reactants were kept under nitrogen at room temperature.

The proper amount of the diisocyanate, as a 50% solution in toluene, was then added all at once at room temperature and the exothermic adduct prepolymer formation was moderated as required to keep the reactants from exceeding 75° C. The reactants were agitated under a stream of dry nitrogen and maintained at 70° C. to 75° C. for a period of 4 hours, and transferred to a dry nitrogen flushed container after this period of time. After at least 24 hours had elapsed, the NCO-terminated prepolymers were then analyzed for % NCO by the dibutlyamine method. (ASTM D4666-87). Table 2 shows reactant concentrations, % NCO content based on 100% solids, and calculated and theoretical values for % NCO. In all cases the diisocyanate charge represents 2 equivalents of NCO per equivalent of the hydroxyl copolyether precursor.

TABLE 2

Charge Ratios and % NCO Contents for Prepolymers R and S

| Ingredients, gm | Prepolymer R | Prepolymer S |
|---|---|---|
| PLURACOL V-7 | 500.0 | 0 |
| UCON 75-H-90,000 | 0 | 500.0 |
| MPEG 5,000 | 0 | 0 |
| Toluene, total | 546.0 | 518.0 |
| IPDI | 45.6 | 0 |
| DESMODUR W | 0 | 17.5 |
| T-12 (~20 ppm) | 0.011 | 0.010 |
| Analysis, % NCO | | |
| Actual (100% solids) | 1.63 | 0.52 |
| Theoretical, calculated | 1.58 | 0.54 |

The above-described Prepolymers R and S correspond to catalyzed versions of P, and O (Table 1) and were prepared as 50% solutions in toluene. PLURACOL-V7 (BASF CORP.) is a trifunctional copolyether which was used as the prepolymer precursor for R, and comprises a 75/25%, by weight, random EO/PO polyether adduct of trimethylolpropane having a OH No. of ≅23.0, and a calculated EW≅2340. The prepolymer adducts were subsequently diluted to about 25%, by weight, of solids, with more toluene and an aliquot thereof was stored at 20° C. to 25° C. for a period of at least 4 months. Both prepolymers remained stable over this period of time and showed no evidence of gelation, indicating an extended shelf stability despite the presence of tin catalyst. For coating of catheters, balloons and other medical devices, the toluene solutions of the hydrophilic prepolymers were further diluted in suitable co-solvents, to a solids content of 2%, by weight, for example, before proceeding to the coating step. According to the % NCO analysis recorded for the above prepolymers, the isocyanate reaction proceeded to completion when catalyzed even at very low tin catalyst levels which were found not to impair biocompatibility for the catheter devices.

Example 5
Evaluation of PU/UV Hydrogels and Commingled Hydrogels

For the purpose of evaluating the PU/UR hydrogel coatings and, in particular, the combination of commingled hydrogel coatings from PU/UR hydrogels and dissimilar hydrogels, according to the present invention, from which the exhibition of excellent lubricity, wear performance, and durability when contacted with body fluids is required, it was decided to deposit the coatings on plasma-treated plastic substrates which were known to have only a limited capability to result in durable covalent bond fixation in the absence of pretreatments. Typical application in the medical devices field comprise the low friction coatings of catheter balloons and other catheter components which are used in coronary angioplasty, where the devices must not only resist excessive wear and maintain permanence during transfer through blocked blood vessels but must also exhibit excellent lubricity while traversing obstructions, and often demand complex handling during manipulations of the device during clinical use. Consequently, initial coating tests were undertaken with PET, PE and HYTREL substrates which are often used as materials of construction for such devices, or portions thereof. For that purpose, it was first decided to utilize test parisons of ammonia plasma-treated PET tubing having dimensions of approximately 6 to 8 inch length, 0.07 to 0.095 inch OD, and 0.04 to 0.07 inch ID, as well as oxygen and ammonia plasma-treated parisons from various PE substrates having the same dimensions. For the evaluation of many characteristic PU hydrogel coatings of the present invention having various compositions as described in Examples 1, 2 and 4, and the commingled hydrogel coatings of the present invention, suitable plasma-treatment parameters, as already described in Example 3, were utilized.

For the establishment of suitable comparison drag force testing, the plasma treatment for this particular analysis protocol was kept constant and included exposing the parisons in the HIMONT Plasma Science 0350 Unit to an initial vacuum of 0.01 Torr followed by application of the ammonia gas plasma at a gas flow rate of 650 ml/min, at a power input of 400 watts and a frequency of 13.56 MHz, at a temperature of from 25° to 40° C., for a period of 3 minutes. The plasma-treated parisons were used within a period of from one to three weeks to eliminate anomaly due to possible fading of the plasma treatment with extended age. The Hydrophilic PU prepolymers, or the tin-catalyzed PU polymer concentrates in toluene, were diluted with MEK to a solids content of 2%, by weight, and the parisons were dip-coated by insertion therein for a period of 30 seconds, and allowed to dry in a forced air hood at room temperature. Next, after an elapsed time of 30 minutes, the resulting PU/UR coated parisons were dip-coated in an aqueous solution of the second dissimilar hydrogel systems which also contained the appropriate tertiary amine or diamine chain-extender catalysts dissolved therein, if desired, to speed up the final hydrogel entanglement between the two, or more, dissimilar polymer species. In the case of uncatalyzed exposure in the aqueous solution of the second coating of the dissimilar hydrogel polymer(s), the double-coated parisons were removed and exposed to an atmosphere of about 50% relative humidity for 72 hours, at room temperature, and then post-cured in a vacuum oven, maintained at a temperature of from about 60° C. to about 70° C., for a period of from about 1 to 2 hours, before being tested in the INSTRON drag force testing fixture described previously. When the aqueous solution of the dissimilar hydrogel polymer contained diamine chain-extenders, or tertiary amine catalysts, the parisons were tested about 24 hours after application of the aqueous dip-coating to the PU/Urea coated parisons. The drag forces (gm) were recorded after 1, 5, 20 and 40 strokes in defibrinated bovine blood as the contact medium. It had previously been determined that blood is much more aggressive than saline solutions, for example, Ringer's Solution, or water, both of which have heretofore been traditionally employed for performance and durability testing in the catheter art. Table 3 shows drag force test results from averages of at least 3 specimens tested in defibrinated bovine blood.

TABLE 3

Drag Forces Tests of Coated PET Parisons in Blood
DRAG FORCE in gm at NUMBER OF CYCLES (1, 5, 20, and 40)

| SAMPLE TYPE | STROKE - 1 | STROKES - 5 | STROKES - 20 | STROKES - 40 |
|---|---|---|---|---|
| NH$_3$-treated Parisons PET | | | | |
| SILICONE MDX4-4159 | 40 | 45 | 155 | >300 |
| HYPOL PreMA ® G-50 | 85 | 90 | 90 | 120 |
| E | 98 | 132 | 152 | 164 |
| R | 80 | 92 | 97 | 110 |
| S | 85 | 100 | 125 | 135 |
| G-50 + HA[1] (no cat.) | 33 | 49 | 72 | 81 |
| G-50 + POLYOX 100M[2] | 40 | 46 | 56 | 61 |
| G-50 + POLYOX 4 MM[3] | 42 | 45 | 53 | 60 |
| R + HA (0.2% EDA) | 38 | 38 | 47 | 56 |
| R + HA (0.1% EDA) | 43 | 56 | 62 | 66 |
| R + POLYOX 100M[4] | 80 | 82 | 96 | 98 |
| R + ALGINIC ACID[5] | 37 | 48 | 75 | 90 |
| R + CARRAGEENAN[6] | 39 | 46 | 72 | 85 |
| S + HA (0.2% EDA) | 63 | 80 | 88 | 99 |
| S + ALGINIC ACID[7] | 45 | 57 | 79 | 95 |
| S + POLYOX 4 MM[8] | 65 | 70 | 79 | 85 |
| Untreated Parisons PET | | | | |
| HYPOL PreMA ® G-50 | 77 | 79 | 91 | 105 |
| R | 75 | 82 | 87 | 98 |
| S | 78 | 82 | 89 | 104 |
| G-50 + HA | 52 | 75 | 90 | 105 |
| G-50 + POLYOX 100M[9] | 51 | 96 | 106 | 112 |
| G-50 + POLYOX 4MM[10] | 50 | 93 | 101 | 110 |
| R + HA (no cat.) | 52 | 77 | 90 | 118 |
| S + HA (no cat.) | 63 | 78 | 85 | 115 |
| R + ALGINIC ACID[11] | 68 | 79 | 93 | 125 |

Note: Specimens showing drag forces of >300 gm in blood bind in fixture during test.
[1]Hyaluronic acid, sodium salt; SIGMA CHEMICAL COMPANY, from Bovine Trachea; 1% aqueous solution of Na salt, containing 0.2%, by weight, of ethylenediamine (EDA).
[2]POLYOX WSR N10 - NW ≅ 100,000 (UNION CARBIDE CORP.); 1% aqueous solution; containing 0.2%, by weight, of EDA.
[3]POLYOX WSR-301 - MW ≅ 4,000,000 (UNION CARBIDE CORP.); 0.25% aqueous solution; containing 0.2%, by weight, of EDA.

TABLE 3-continued

Drag Forces Tests of Coated PET Parisons in Blood
DRAG FORCE in gm at NUMBER OF CYCLES (1, 5, 20, and 40)

| SAMPLE TYPE | STROKE - 1 | STROKES - 5 | STROKES - 20 | STROKES - 40 |
|---|---|---|---|---|

[4]Uncatalyzed aqueous WSR N10 hygrogel polymer system.
[5]Sodium Alginate (SIGMA CHEMICAL COMPANY); low viscosity 2% aqueous solution; containing 0.2%, by weight, of EDA.
[6]Type IV Lambda Carrageenan; sodium salt (SIGMA CHEMICAL COMPANY); 1% aqueous solution; containing 0.15%, by weight, of EDA.
[7]Same compound and EDA catalyst level as 5.
[8]POLYOX WSR-301; 0.25% aqueous solution containing 0.15%, by weight, of EDA.
[9]No amine catalyst added for hydrogel formation.
[10]No amine catalyst added for hydrogel formation.
[11]No amine catalyst added for hydrogel formation.

Similar experiments were run in a few instances with plasma-treated coatings deposited on parisons made from HYTREL® and in general similar results were observed. The experiments show that the "Silicone" coating gives very good results upon starting of the initial tests, but loses its lubricity very quickly when exposed to blood as the contact medium. The PU/PUR hydrogels and particularly also the PU/PUR hydrogels which are commingled with one, or more, of the dissimilar hydrogels, prepared in accordance with the present invention, showed particularly good permanence and lubricity in the presence of blood as the medium. These phenomena, however, are unexpected and are not predictable based on the feel of the coatings when touched, since the "Silicone" coating feels very "slippery" when first touched, but loses its efficacy completely during the test in bovine blood. It is also important to note that various combinations of surface treatments of high and low density polyethylenes, which render the polyethylenes hydrophilic, and the influence of ammonia plasma or gaseous ammonia, which affix amino groups on the substrates, unexpectedly give excellent adhesion and permanence in blood. Typical polyethylene treatments which are favored include, for example, oxygen-containing plasma treatment of substrates, either with pure oxygen, air or water-vapor, or combinations thereof, or a mixture of oxygen and argon, followed by a second plasma treatment comprising ammonia, to render the material hydrophilic as well as having amino groups affixed thereto. Still another treatment version which is similarly effective consists of first treating polyethylene with an oxidative chemical treatment followed by the application of an ammonia plasma treatment to make the substrate quite hydrophilic and bearing reactive amino groups according to ESCA surface analysis. Moreover, it is also observed that surface hydrophilicity and attachment of amino groups is also achieved by means of first plasma-treating such PE substrates by means of oxygen plasma followed immediately by the application of gaseous ammonia as a post-stream. All these various methods unexpectedly result in good adhesion and permanence characteristics for the commingled hydrogels in blood, when the hydrogels are made from the very hydrophilic PU/PUR "tie-coats" of the present invention. The commingled hydrogel polymers of the present invention also exhibit very good permanence characteristics apparently because of the excellent bonding to the ammonia plasma-treated PET and HYTREL in the case of the various very hydrophobic polyethylenes, oxygen treatment alone gives unsatisfactory results with the relatively slow-reacting hydrophilic PU prepolymers of the present invention. Preliminary experiments with ammonia plasma-treated substrates, such as TPU and hydrophobic nylons, have also shown good results. Hence, it appears feasible to treat various plastic substrates for medical devices, such as catheters, in like manner to facilitate the process methods and make them more cost-effective.

Example 6

Comparative Test of Inventive and Prior Art Coatings in Several Media

Very surprisingly, the hydrophilic hydrogels affixed to plasma-treated surfaces according to the present invention showed no unusual results when tested in media typically utilized by others to test the properties of low friction coatings. Previous commercial materials had usually been tested in water, or Ringer's Solution. The efficacy of the covalently bonded PU/PUR hydrogels and the combination of commingled hydrogel coatings from covalently bonded PU/PUR hydrogels commingled with one, or more, dissimilar hydrogel polymers, was comparatively tested in the presence of water, Ringer's solution and defibrinated bovine blood. Dynamic testing of PET parisons was conducted in the presence of bovine blood to determine whether there existed unusual interactions between commercially available coatings and the coating based on PU hydrogels, as well as the coatings combinations of the commingled hydrogel systems of the present invention.

The results are presented in Table 4:

TABLE 4

Comparison Drag Force Tests in Various Media
Drag Force in gm at Number of cycles

| PET PARISON TEST MEDIUM | STROKE - 1 | STROKES - 5 | STROKES - 20 | STROKES - 40 |
|---|---|---|---|---|
| | Drag Force in gm at Number of Cycles (1, 5, 20, 40) | | | |
| Uncoated PET | | | | |
| Water | 142 | 150 | 160 | 160 |
| Ringer's Solution | 70 | 75 | 75 | 75 |

TABLE 4-continued

Comparison Drag Force Tests in Various Media
Drag Force in gm at Number of cycles

| PET PARISON TEST MEDIUM | STROKE - 1 | STROKES - 5 | STROKES - 20 | STROKES - 40 |
|---|---|---|---|---|
| Blood Untreated PET "Silicone" Coating | 230 | 220 | 220 | 220 |
| Water | 45 | 40 | 44 | 45 |
| Ringer's Solution | 59 | 59 | 60 | 60 |
| Blood PLASMA-TREATED PET (NH$_3$) HYPOL PreMA ® G-50 | 45 | 165 | 225 | >300 |
| Water | 100 | 100 | 100 | 100 |
| Ringer's Solution | 54 | 54 | 67 | 75 |
| Blood "Silicone" Coating | 77 | 79 | 91 | 105 |
| Water | 35 | 40 | 43 | 45 |
| Ringer's Solution | 55 | 55 | 55 | 60 |
| Blood G-50 + HA (EDA) | 35 | 155 | 230 | >300 |
| Blood R + HA (EDA) | 33 | 49 | 72 | 81 |
| Blood S + POLYOX 4 MM | 43 | 56 | 62 | 66 |
| Blood R + POLYOX 100M | 65 | 70 | 79 | 85 |
| Blood | 80 | 82 | 96 | 98 |

Note: Specimens registering drag forces of >300 gm bind in fixture during testing.

The above comparative tests illustrate that the uncoated PET parisons when tested in the test fixture previously described herein exhibited relatively high drag forces in water, low drag forces in Ringer's isotonic saline solution, and consistently high drag forces in blood. The "Silicon" coating gave low drag forces in both water and saline resulted in only marginal improvement with respect to lubricity and, particularly, with regard to wear resistance when tested in blood. Although it is known from ESCA studies that ammonia plasma treatment affixes substantial amounts of reactive amino groups onto very hydrophobic polymers such as polypropylenes and other hydrophobic synthetic polymers containing at least substantial amounts of labile hydrogen atoms attached to tertiary carbon atoms (ESCA analyses for amino surface groups), these findings appear not to hold when various polyethylenes are exposed to such ammonia plasma treatments. Consequently, the present series of experiments was implemented to define better methods to make the present process more effective for polyethylene polymers and other very non-polar and hydrophobic substrates, such as for example, nylon 11 and nylon 12, among others. It has now been observed that polyethylenes can be exposed to oxidative surface treatments or oxygen-containing plasma treatments followed by subsequent treatments with ammonia in the presence of plasma, or optionally, as a gaseous post-stream without use of plasma, to yield polar and hydrophilic PE substrate surfaces having highly reactive amino functional groups attached to their surfaces. Such highly polar, hydrophilic, and amino group-bearing reactive surfaces are highly capable of forming covalently attached PU/PUR hydrogels on such treated polyethylene surfaces.

For the purpose of this experimental program, low density polyethylene parisons, having an ID of about 0.066", an OD of about 0.09", and a length of from about 6" to 8" were treated with various oxidative surface treatments under the conditions set forth in Table 5, dip-coated with 2 to 4% solutions of Prepolymer R of Example 4, which had been prepared as a 25% solution in toluene in methylethyl ketone. The parisons were dip-coated in the MEK/toluene solutions for a period of about 30 seconds, and allowed to dry by hanging them in a forced air hood at room temperature for about 20 minutes. The parisons were then exposed overnight on top of an open water-bath having a water temperature of about 35° C. to facilitate transformation and cure of the resulting PU/PUR hydrogel. The parisons were further post-cured in a vacuum oven at 60° C. for 1 hour. The coating procedure was conducted within one day after the final plasma or gaseous post-stream treatment, and the instron test with the abrasive SCRUNGE® test pad was performed within 72 hours after leaving the coated parison under ambient conditions at room temperature. The SCRUNGE® test pads and test fixture were similar to the ones described above and the test medium consisted of fresh citrated cow blood. The drag force measurements were conducted on an Instron Model 4201, equipped with a 20 lbs load cell. For the purpose of the various tests conducted under different treatment conditions, two coated parisons were tested for each condition. The data presented represent averages of two tests, running the uncoated specimens first, followed by the coated specimens. The drag force ratio was calculated by averaging drag force results of two coated runs, then dividing them by the uncoated drag force results at the same number of strokes. Table 5 shows the drag forces in gm's, the drag force ratios at 1, 5, 10 and 15 stroke cycles, and notes the corresponding oxidative and treatment conditions of the PE parisons:

present invention are readily reactivated within from 15 seconds to no longer than 1 to 2 minutes, by immersion in Ringer's Solution at room temperature. Upon subsequent

TABLE 5

Drag Force in gm and Drag Force Ratio of Coated/Untreated PE Parisons at 1, 5, 10 and 15 Cycles

| | | | STROKE CYCLE | | | | | | |
|---|---|---|---|---|---|---|---|---|---|
| | | | 1 | | 5 | | 10 | | 15 |
| Plasma 1[1] | Plasma 2[2] | Post-Stream[3] | Drag Force, gm | Ratio[4] | Drag Force, gm | Ratio[4] | Drag Force, gm | Ratio[4] | Drag Force, gm | Ratio[4] |
| $O_2$ | $NH_3$ | None | 75 | 0.64 | 89 | 0.67 | 94 | 0.74 | 93 | 0.73 |
| $NH_3/O_2$ | None | $NH_3$, 5 min | 74 | 0.41 | 91 | 0.47 | 97 | 0.52 | 102 | 0.56 |
| $NH_3/O_2$ | $O_2$ | None | 65 | 0.44 | 89 | 0.57 | 95 | 0.62 | 98 | 0.67 |
| $Ar/O_2$ | $O_2$ | $NH_3$, plasma | 52 | 0.47 | 74 | 0.59 | 83 | 0.69 | 86 | 0.73 |
| $Ar/O_2$ | None | $NH_3$, 5 min | 76 | 0.42 | 91 | 0.52 | 100 | 0.59 | 104 | 0.62 |

[1]Plasma 1: RF input power = 400 watts
[2]Plasma 2: RF input power = 200 watts
[3]Plasma conditions: Plasma duration: 2 min; Gas flow rate for $NH_3$ = 600 ml/min; gas flow rate for $O_2$ = 100 ml/min; gas flow rate for $NH_3/O_2$ = 250 ml/min, gas flow rate ratio for $NH_3/O_2$ = 1.5; gas flow rate for $Ar/O_2$ = 710 ml/min, gas flow rate ratio for $Ar/O_2$ = 6.1
[4]Ratio: Force (coated)/Force (untreated) at the same number of cycles;
Note: Unless all the Instron data are measured the same day, slight problems of parison and test fixture alignment on the Instron, variations in the quality and age of blood can be experienced, all of which can affect drag force measurements quite considerably. Consequently, during these experiments control tests with coated specimens as well as non-coated, non-treated parisons were always performed, and the results have been expressed as drag force ratios to minimize the scattering and maximize the accuracy of the data.

The above data show various combination treatments of polyethylene substrates with oxidizing plasma treatments of the substrates with oxygen or argon plus oxygen, followed by concurrent or subsequent treatments with ammonia plasma gases or gaseous ammonia as a post-stream treatment. All these combinations of treatments result in final coated substrates which behave favorably with respect to wear performance in blood of the hydrophilic PU/PUR hydrogel coatings of the present invention. Due to the lack of reactivity of the cycloaliphatic isocyanate moieties in isophorone diisocyanate and other cycloaliphatic diisocyanates, the response is not positive unless highly active amino groups are also affixed to the PE substrate surfaces which have been made more polar and hydrophilic. Similar initial results have been observed with nylons 11 and 12, both of which are relatively hydrophobic polymers used in catheters.

Example 8
Drying, Sterilization and Reactivation of Coatings

After the preparation of the final hydrogel which is covalently bonded to the nitrogen containing plasma-treated substrate, or to an aminosilane coated metal part, medical devices coated with coatings of the present invention are preferably dried, packaged in materials which are not moisture-permeable, and sterilized before use under clinical conditions. Drying of the device requires complete evaporation of the water from the hydrogel barrier coating. Because the dry hydrophilic TPU base hydrogel is elastomeric, the coating does not flake or crack during drying. This can be accomplished by vacuum-drying of the apparatus under conditions well known in the art. After drying, the apparatus can be heat-sealed inside a moisture-proof plastic film, and sterilized, for example, by γ-radiation, or other means, to sterilize the medical device. The device can be stored and shipped thereafter, and it can be rehydrated with saline solution, or other means, just before clinical use. Preliminary tests have shown that the hydrogels of the present invention are readily reactivated within from 15 seconds to no longer than 1 to 2 minutes, by immersion in Ringer's Solution at room temperature. Upon subsequent measurement of the dynamic drag force in blood, excellent low initial force readings were restored.

What is claimed is:

1. A medical device comprising an organic polymer substrate material having a coating thereon, the coating comprising an interpenetrating network of two different hydrogel polymers, one of which is a polyurethane/polyurea hydrogel polymer, the polyurethane/polyurea hydrogel polymer being linked to the substrate material by covalent urea linkages.

2. A device as in claim 1 wherein the second of said two hydrogel polymers is selected from the group consisting of polysaccharide polymers, metal salts of polysaccharide polymers, poly(ethylene oxide)homopolymers and poly(N-vinylpyrrolidone)polymers.

3. A device as in claim 1 wherein said substrate material is selected from the group consisting of polyethylene terephthalate, polyether-polyester block copolymers, polyether-polyamide block copolymers, polyamide, polyimides, polyurethanes, polyofin polymers, hydrocarbon elastomers, nitrile rubbers, ethylene/alkyl acrylate copolymers and natural rubber.

4. A device as in claim 1 formed by a process comprising the steps of:
 a) providing the substrate material with isocyanate-reactive chemical groups on the surface thereof, at least some of which are amine groups;
 b) forming a tie-coat layer by applying a first formulation to the substrate surface, the first formulation comprising an isocyanate functional hydrogel-forming prepolymer formed by reaction of a polyether and a polyisocyanate compound,
whereby some of the isocyanate groups of the prepolymer react with said amine groups to form urea linkages between the substrate material and the prepolymer and some of the isocyanate groups of the prepolymer remain unreacted; and
 c) applying a second formulation to the tie-coat layer, the second formulation having therein at least one isocyanate-reactive component and comprising an aqueous solution of a second hydrogel polymer different from said polyurethane/polyurea hydrogel polymer, whereby water in the second formulation forms a hydrogel with tie-coat layer prepolymer; the second hydrogel polymer penetrates into the tie-coat layer; and the free isocyanate groups of the tie-coat layer prepolymer react with said isocyanate-reactive component in the second formulation to form said polyurethane/polyurea hydrogel polymer, such that at least a portion of the tie-coat layer and the barrier layer are commingled and form said interpenetrating network of polyurethane/urea and second hydrogel polymers.

5. A device as in claim 4 wherein said amine groups were provided on substrate material surface by treatment thereof with a plasma of a nitrogen-containing gas.

6. A device as in claim 4 wherein said second hydrogel polymer is a poly(N-vinylpyrrolidone)polymer.

7. A device as in claim 1, the device being a catheter, a catheter balloon or a stent.

* * * * *